US009833579B2

(12) United States Patent
Pedersen et al.

(10) Patent No.: US 9,833,579 B2
(45) Date of Patent: Dec. 5, 2017

(54) MEDICAL INJECTION DEVICE

(75) Inventors: Simon Munch Pedersen, Copenhagen N (DK); Bo Radmer, Hilleroed (DK); Jesper Peter Windum, Hilleroed (DK); Soeren Dyring Jensen, Valby (DK); Christian Plambech, Soeborg (DK); Christian Hoejris Nielsen, Copenhagen NV (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 13/817,708

(22) PCT Filed: Aug. 19, 2011

(86) PCT No.: PCT/EP2011/064325
§ 371 (c)(1),
(2), (4) Date: May 3, 2013

(87) PCT Pub. No.: WO2012/022810
PCT Pub. Date: Feb. 23, 2012

(65) Prior Publication Data
US 2013/0211330 A1    Aug. 15, 2013

Related U.S. Application Data

(60) Provisional application No. 61/377,294, filed on Aug. 26, 2010.

(30) Foreign Application Priority Data

Aug. 19, 2010    (EP) .................................... 10173411

(51) Int. Cl.
A61M 5/32        (2006.01)
A61M 5/24        (2006.01)
(Continued)

(52) U.S. Cl.
CPC ........ *A61M 5/3297* (2013.01); *A61M 5/2033* (2013.01); *A61M 5/326* (2013.01);
(Continued)

(58) Field of Classification Search
CPC .............. A61M 5/3243; A61M 5/3297; A61M 5/3257; A61M 5/3269; A61M 2005/3263; A61M 2005/3261
(Continued)

(56) References Cited

U.S. PATENT DOCUMENTS 2,752,918 A    7/1956    Uytenbogaar
3,136,313 A    6/1964    Enstrom et al.
(Continued)

FOREIGN PATENT DOCUMENTS

AT    007347 U1    2/2005
DE    3527066 A1    2/1986
(Continued)

*Primary Examiner* — Bhisma Mehta
*Assistant Examiner* — Jenna Zhang
(74) *Attorney, Agent, or Firm* — Wesley Nicolas

(57) ABSTRACT

The present invention relates to medicament injection devices (100). A cartridge (600) with a septum and a needle unit (500) having front and rear needles (510, 520) are configured for relative movement from a state where the septum is sealed to a state where the septum is pierced by the rear needle (520). The injection device (100) may include a needle shield (350) and be configured for piercing the septum by the rear needle (520) when the front needle (510) is operated relative to the needle shield (350). The injection device (100) may also include a damping mechanism configured for limiting the speed of movement of the cartridge relative to the needle unit. The injection device (100) may also include an indicator generating a signal when a piston driver has travelled the complete stroke length, wherein the
(Continued)

Figure 1A:
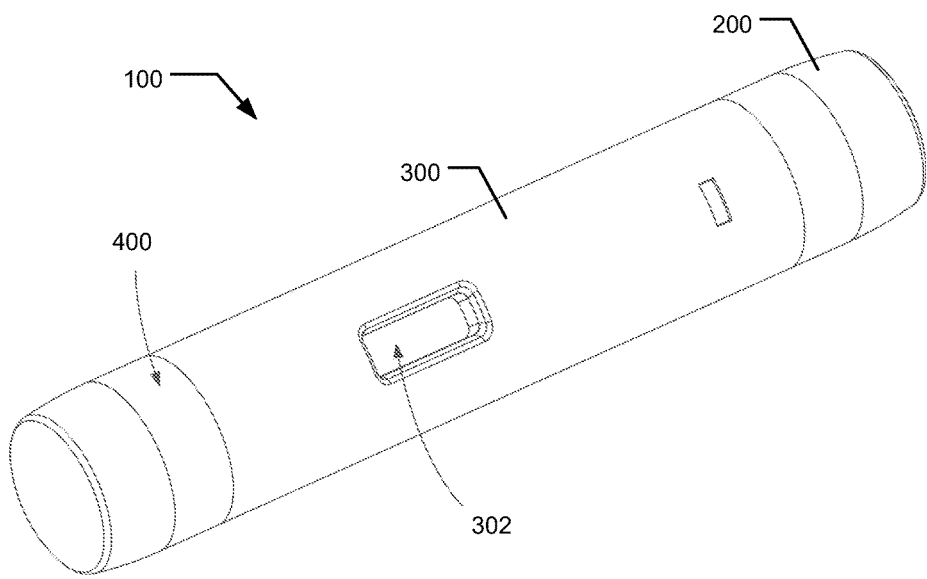

indicator has a deflection element that is deflected prior to or during movement of the cartridge relative to the housing.

12 Claims, 13 Drawing Sheets

(51) Int. Cl.
    *A61M 5/50* (2006.01)
    *A61M 5/20* (2006.01)
    *A61M 5/48* (2006.01)

(52) U.S. Cl.
    CPC ........ *A61M 5/3287* (2013.01); *A61M 5/5086* (2013.01); *A61M 5/482* (2013.01); *A61M 5/484* (2013.01); *A61M 2005/2013* (2013.01); *A61M 2005/3247* (2013.01); *A61M 2005/3267* (2013.01); *A61M 2205/581* (2013.01); *A61M 2205/582* (2013.01)

(58) Field of Classification Search
    USPC .................................. 604/198–201, 204–206
    See application file for complete search history.

(56) References Cited

U.S. PATENT DOCUMENTS

| | | | |
|---|---|---|---|
| 4,378,015 A | | 3/1983 | Wardlaw |
| 4,717,383 A | | 1/1988 | Phillips et al. |
| 5,176,643 A | * | 1/1993 | Kramer ............... A61M 5/2033 604/135 |
| 5,658,259 A | * | 8/1997 | Pearson ............... A61M 5/2033 604/136 |
| 6,203,529 B1 | * | 3/2001 | Gabriel ............... A61M 5/3202 604/192 |
| 6,210,369 B1 | * | 4/2001 | Wilmot ............... A61M 5/2033 604/157 |
| 6,258,068 B1 | | 7/2001 | Kirchhofer et al. |
| 6,743,203 B1 | * | 6/2004 | Pickhard ............... A61M 5/002 604/110 |
| 7,449,012 B2 | | 11/2008 | Young et al. |
| 7,611,491 B2 | | 11/2009 | Pickhard |
| 7,717,877 B2 | | 5/2010 | Lavi et al. |
| 8,632,504 B2 | * | 1/2014 | Young ................. A61M 5/2033 604/135 |
| 2002/0007671 A1 | * | 1/2002 | Lavi ....................... A61M 5/19 73/149 |
| 2003/0078546 A1 | * | 4/2003 | Jensen ................. A61M 5/3202 604/232 |
| 2003/0144633 A1 | | 7/2003 | Kirchhofer |
| 2005/0038392 A1 | * | 2/2005 | DeSalvo ............. A61M 5/3243 604/198 |
| 2007/0017533 A1 | | 1/2007 | Wyrick |
| 2007/0073232 A1 | * | 3/2007 | Pickhard ............. A61M 5/2033 604/134 |
| 2007/0219498 A1 | | 9/2007 | Malone et al. |
| 2007/0275338 A1 | * | 11/2007 | Acker ................. C03B 33/0235 432/8 |
| 2007/0276338 A1 | * | 11/2007 | Shue .................... A61M 5/3202 604/187 |
| 2009/0312705 A1 | | 12/2009 | Grunhut et al. |
| 2011/0301548 A1 | * | 12/2011 | Young ................. A61M 5/2033 604/200 |

FOREIGN PATENT DOCUMENTS

| | | | | |
|---|---|---|---|---|
| EP | 1782854 A2 | | 5/2007 | |
| GB | 2467904 A | * | 8/2010 | .......... A61M 5/2033 |
| GB | 2467904 B | * | 6/2013 | .......... A61M 5/2033 |
| JP | 2007503853 A | | 3/2007 | |
| WO | 94/07553 A1 | | 4/1994 | |
| WO | 2005/009515 A1 | | 2/2005 | |
| WO | 2005/025636 A2 | | 3/2005 | |
| WO | 2005/070481 A1 | | 8/2005 | |
| WO | 2007/008257 A2 | | 1/2007 | |
| WO | 2008/116688 A1 | | 10/2008 | |
| WO | 2009/100549 A1 | | 8/2009 | |
| WO | 2010/035057 A1 | | 4/2010 | |
| WO | 2010/035059 A1 | | 4/2010 | |

* cited by examiner

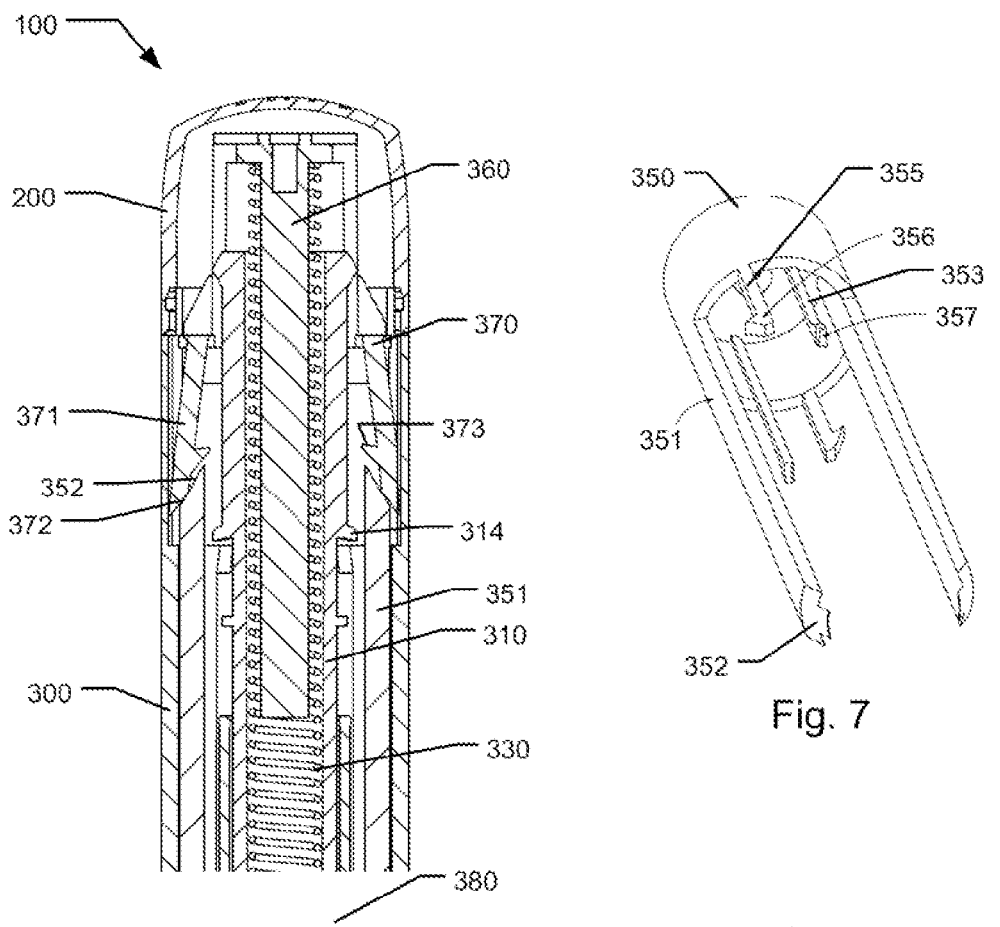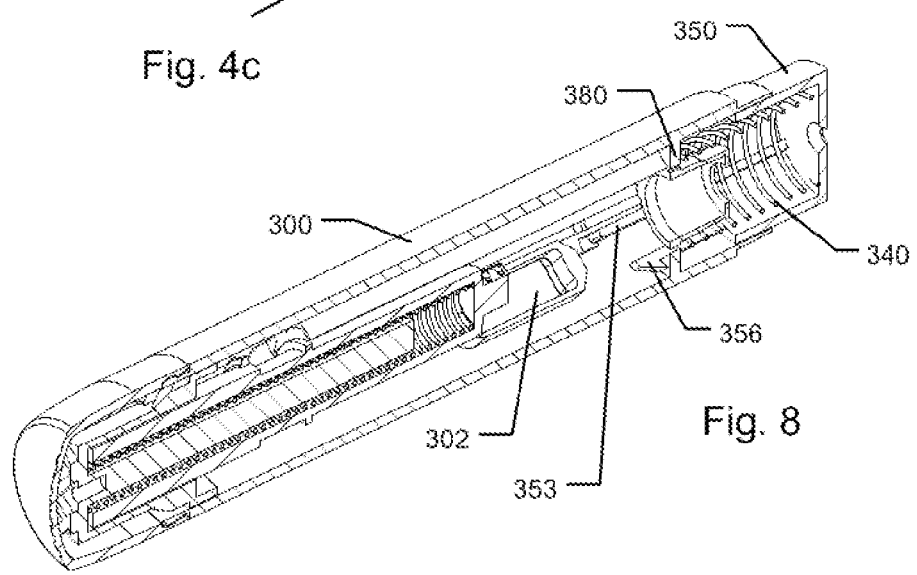

MEDICAL INJECTION DEVICE

CROSS-REFERENCE TO RELATED APPLICATIONS

This application is a 35 U.S.C. §371 National Stage application of International Application PCT/EP2011/064325 (WO 2012/022810), filed Aug. 19, 2011, which claimed priority of European Patent Application 10173411.9, filed Aug. 19, 2010; this application claims priority under 35 U.S.C. §119 of U.S. Provisional Application 61/377,294; filed Aug. 26, 2010.

FIELD OF THE INVENTION

The present invention relates to injection devices for injecting a medicament. In particular the present invention relates to injection devices for injecting a medicament from a held cartridge and improvements relating to the performance of such injection devices.

BACKGROUND OF THE INVENTION

In relation to some diseases patients must inject a medicament on a regular basis such as once weekly, once daily or even a plurality of times each day. In order to help patients overcome fear of needles, fully automatic injection devices have been developed that makes the use of an injection device as simple as possible. Such devices are typically designed such that a user shall position the injection device onto the injection site and activate the device. Such activation causes the device to insert a needle into the skin, eject a dose of the medicament and subsequently move the needle into a shielded position.

Generally, for injection devices of the above type, main attention has been directed towards devices equipped with a glass cartridge where a needle cannula is fixedly attached to the outlet end of a cartridge. Such needle cannula is initially being covered in a sterile way by a cap member that during storage acts as a stopper for the needle cannula, and which requires removal prior to use. Typically, these devices further include a needle shield portion for shielding the needle before and/or after use. Disclosure of such devices is included in U.S. Pat. No. 7,449,012, U.S. Pat. No. 7,717,877 and WO2008/116688.

Some manufacturers prefer the type of cartridge having a pierceable septum which during storage provides a seal for the cartridge outlet and where the septum, upon use, is pierced by a needle cannula. Prior art devices using this type of cartridge are disclosed in U.S. Pat. No. 2,752,918, U.S. Pat. No. 5,658,259, U.S. Pat. No. 6,743,203, U.S. Pat. No. 6,210,369 and WO94/07553. Devices of that type hold a needle assembly and a cartridge in a separated storage configuration which upon activation of the device allows for subsequent connection to establish fluid communication between cartridge and needle assembly. In addition, automatic penetration of the needle into the skin of the user for subsequent automatic delivery of the medicament is typically incorporated.

While the above devices aim at providing a high level of automation, injection devices that provide automatic insertion of the needle into the dermis also prevent the user from controlling the insertion, which can lead to uneasiness for the user. In WO2008/116688, whilst providing manual control for insertion of the needle by means of a needle shield which is moved relative to the needle, the disclosed type of device still utilize the type of cartridge having an integrated needle cannula.

Injection devices that provide automatic delivery of the medicament, i.e. auto-injectors, typically use a spring as driving force for the injection. Before use, the driving spring will be held in a pre-tensioned position from which it is released upon activation of the device. After activation the spring uses the energy from the tension to drive forward the piston of a cartridge.

One problem associated with auto-injectors is that the piston is moved forward, the tension of the spring decreases which in turn decreases the force of the spring pressing on the piston. When using auto-injectors it is important to have a clear feedback communicating to the user when the injection is finished in order to prevent the user from removing the device from the injection site prematurely. WO 2010/035057 and WO 2010/035059 disclose auto-injectors that provide an audible end of dose confirmation. However, these solutions are somewhat problematic in that the energy used to provide the audible feedback is required near the end of the injection where the spring force available for driving the injection is at a minimum. This sets a limit for the amount of energy which can be used to provide feedback to the user as the dosing force and friction forces in the cartridge/syringe also must be overcome.

A different approach is disclosed in WO 2005/070481 wherein the device may include two arms that are pre-tensioned during assembly of the device and where the pre-tensioned arms are released momentarily when the device enters the end of dose condition to generate a click sound. However, devices wherein parts remain in a tensioned state during storage generally leads to creep of the material which generally results in a non-optimal performance.

Still other problems are associated with auto-injectors that use a medicament cartridge and a needle assembly that during storage is kept in a separated configuration. Connecting the cartridge and needle is in many cases done by using the dose mechanism to move the cartridge forward thus allowing the needle to penetrate the sterile barrier of the cartridge. As the dose mechanism often comprises a pre-tensioned spring this means that the initial relaxation of the spring is used to move the cartridge in contact with the needle. As the spring must be able to overcome forces acting against it while ejecting the medicament, e.g. friction, the spring force needs to be sufficiently high to move the plunger within the cartridge even near the end of the dosing movement. As the pre-tensioned spring provides the highest force at the start of the dose, this means that the highest force provided by the spring is used to move the cartridge into contact with the needle. Moving the cartridge into contact with the needle requires considerably less force than what is required for ejecting the medicament, which means that the cartridge is subjected to a high force and therefore moved into contact with the needle at a high speed. As the cartridge reaches its contact point with the needle it is stopped mechanically. Because of the high speed of movement this stop will emit a considerable amount of noise which can be heard by the user.

This sound can cause uneasiness with the user, thus resulting in decreased confidence toward the product. US2007/0219498 includes disclosure of a device which includes a stationary shock absorber to reduce dynamic stresses on internal components.

Having regard to the above-identified prior art devices, it is an object of the present invention to provide an injection device which enables improved control of the device during operation.

A further object of the invention is to provide an injection device, which provides an improved end of dose indication feature.

A further object of the invention is to provide an injection device which performs more quietly during the initial stages of operation.

Yet additional further objects of the invention are to provide measures for obtaining devices having a superior performance and, at the same time, enabling manufacture at a reduced cost.

BRIEF DESCRIPTION OF THE INVENTION

In a first aspect, the present invention relates to an injection device comprising:

a) a medicament cartridge having a cartridge septum adapted to be pierced by a needle for establishing fluid communication with the cartridge interior and having a slideably arranged piston which is driveable towards the cartridge septum, b) a piston driver capable of driving the piston towards the cartridge septum, c) a needle unit having a front needle for penetrating the skin of a subject user and a rear needle for piercing the cartridge septum, the cartridge and the rear needle being configured for relative movement from a first state where the cartridge septum is sealed to a second state where the cartridge septum is pierced by the rear needle, d) a needle shield associated with the needle unit, the needle shield and the front needle being configured for relative movement from a shielded state where the front needle is shielded into an unshielded state where the front needle protrudes from the needle shield, and e) a holding mechanism associated with to the needle unit and the cartridge for releasably maintaining the needle unit and the cartridge in the first state, the holding mechanism being configured to be released upon the front needle being shifted from the shielded state to the unshielded state.

In the injection device according to the first aspect, the front needle is configured to be manually operable relative to the needle shield such that when the needle shield is held against an injection site, manual operation of the front needle relative to the needle shield or vice versa causes manual penetration of the front needle into the injection site and causes subsequent release of the holding mechanism. Hence, movement between the cartridge and the needle unit is enabled only after the front needle has been brought into the state where the front needle protrudes partly or fully from the exterior of the needle shield.

The definition cited under e), i.e. that the holding mechanism is configured to be released upon the front needle being shifted from the shielded state to the unshielded state is to be construed broadly, meaning that the holding mechanism may be configured to be released at any chosen point in time between the initial state wherein the front needle is fully shielded to the state where the tip of the front needle protrudes furthest from the needle shield.

According to the first aspect of the invention, by configuring the device so that a pushing force exerted manually on a part of the device is transferred to a manual force acting on the needle unit for manual penetration of the front needle into the injection site, the user gains improved control of the insertion of the injection needle. At the same time, by using this configuration the needle is hidden from the user during an administration. By providing an improved control of the needle insertion procedure a potential uneasiness for the user can be alleviated. The first part of the activation movement moves the needle forward relative to the needle shield to insert the needle in the user's skin. The second part of the movement activates the injection mechanism. This allows the user to manually insert the needle before activating the device and an administration may be stopped in time should the user wish to abort the operation.

The needle unit may incorporate a sterility barrier either for the front needle, for the rear needle or for both. In some embodiments, the each of the sterility barriers may be formed as a flexible sheath configured as a closed cavity for accommodating at least a part of the respective ones of the front needle and the rear needle.

In some embodiments the device may include a needle shield spring which is associated with the needle shield and the needle unit to urge the front needle into its shielded state or to urge the needle shield into the state where the front needle is shielded.

In one embodiment the holding mechanism comprises a releasable retainer configured to retain the piston driver relative to the needle unit and configured for release upon relative movement between the needle unit and the needle shield for allowing the piston driver to move relative to the needle unit. In such configuration it is ensured that the piston of the cartridge is only pressed forward after an effective needle penetration into the injection site has been obtained.

Also, in some embodiments, the holding mechanism may be configured for maintaining the rear needle and the cartridge in the first state until the front needle protrudes a predetermined distance from the needle shield. When the front needle protrudes even further from the needle shield than said predetermined distance, the holding mechanism is released for enabling the rear needle and the cartridge to shift into the second state where the rear needle penetrates the cartridge septum.

In further embodiments, the holding mechanism in addition defines a release coupling configured to cause release of said releasable retainer when the front needle protrudes from the needle shield to a greater extent than said predetermined distance.

The injection device may comprise an actuator in the form of an energy source coupled to the piston driver and configured for driving the piston driver upon release of the holding mechanism. The energy source may be provided as a stored energy source, such as a pre-strained spring, a compressed gas etc. In other forms, the energy source is configured to become charged during an initial operation of the device prior to activation of the injection mechanism. In still other embodiments, the actuator may be provided as a device which is manually driveable by the user of the device, e.g. by coupling the manually driveable device with the piston driver or by providing the piston driver as the manually driveable device.

In some embodiments, the actuator may be capable, upon release of the holding mechanism, to cause the cartridge and the rear needle to enter into the state where the cartridge septum is pierced by the rear needle and subsequently to cause the piston driver to move to dispense the medicament through the needle unit.

In particular embodiments, the piston driver is attached to the piston of the cartridge. Such attachment may be provided by a threaded engagement, a snap connection or by various other type of mechanical engagement. In some embodiments the piston driver may even define the piston of the cartridge which at the same time facilitates sealing of the piston relative to the body of the cartridge.

The injection device may incorporate an activator which is mechanically associated with the needle unit so that when the activator and the needle shield is moved relative to each other it causes the front needle and the needle shield to move relative to each other. In some embodiments the needle unit substantially follows movement of the activator as the activator moves relative to the needle shield.

In some embodiments the activator is configured to define a housing section which at least partly accommodates the cartridge and where the housing section is adapted to be gripped by the hand of the user. In such embodiment, the activator may be coupled to the needle unit to transfer a force from the activator to the needle unit when the activator is moved relative to the needle shield.

In alternative embodiments, the needle shield defines a housing section which at least partly accommodates the cartridge and wherein the activator is coupled to the needle unit to transfer a force from the activator to the needle unit when the activator is moved relative to the needle shield. In such an embodiment, the activator may be designed as a push button which extends from the housing section at the end opposite the needle end of the device. A needle shield spring may be associated with the needle shield and the needle unit to urge the front needle into its shielded state. Also, an activator spring may be arranged between the activator and the needle unit to urge the needle unit away from the activator. In such embodiment the spring constant of the activator spring may be greater than the spring constant of the needle shield spring. Hence, by this arrangement, the front needle is adapted to protrude from the needle shield before the activator releases the holding mechanism for enabling relative movement between the cartridge and the needle unit.

According to a second aspect of the invention, an injection device is provided comprising: a) a needle unit comprising a front needle adapted for penetrating the skin of a subject user and a rear needle configured for piercing a cartridge septum, b) a medicament cartridge comprising a cartridge septum adapted to be pierced by the rear needle for establishing fluid communication with the cartridge interior and a slideably arranged piston which is driveable towards the cartridge septum, the cartridge being movably arranged relatively to the needle unit from an initial state where the cartridge septum is not pierced by the needle into a state where the cartridge septum is pierced by the rear needle, c) a piston driver for moving the piston of the cartridge, d) a holding mechanism for releasably maintaining the cartridge in the initial position relative to the needle unit and e) a damping mechanism which is adapted to limit and/or reduce the speed of movement of the cartridge relative to the needle unit.

According to the second aspect, by providing an injection device with a damping mechanism wherein a damping force acts against the movement of the cartridge relative to the needle unit, an injection device is provided where the speed of movement of the cartridge is lowered compared to a similar device not being equipped with such damping mechanism. A decrease in the sound emitted by the impact between cartridge and needle unit will decrease patient discomfort and lessen confusion for the user as no distinct sound is made during the connection operation between the cartridge and the needle. In addition, the risk of damaging the cartridge during its forward movement is lowered as the speed is decreased and the contact forces during connection to the needle unit is decreased.

The needle unit may be provided as a needle assembly wherein a front needle part and a rear needle part are arranged relative to a needle hub.

The cartridge may be configured for movement relative to the rear needle from a first state where the cartridge septum is sealed to a second state where the cartridge septum is pierced by the rear needle.

The holding mechanism may be associated with the piston driver for releasably maintaining the cartridge in an initial position. In one embodiment, the holding mechanism is coupled to the piston driver whereby the piston driver is maintained in an initial position. In one form the piston driver is capable of being released to cause the cartridge to move relatively to the needle unit to enter into the state where the cartridge septum is pierced by the rear needle and subsequently to be moved to dispense the medicament through the needle unit. In one form, the piston driver attaches to the piston of the cartridge.

The damping mechanism may be adapted for operating at least during a part of the movement of the cartridge relative to the needle unit for limiting and/or reducing the speed of movement of the cartridge. In particular forms the damping mechanism limits or reduces the speed of the cartridge relative to the needle unit until a stop geometry limits further movement between cartridge and needle unit. In particular embodiments, the damping mechanism is adapted to provide a damping effect on the piston driver when the cartridge moves relative to the needle unit.

The damping mechanism may be provided by means which provides a counterforce acting against a primary force which drives the cartridge relative to the needle unit. Non-exhaustive examples include friction based dampers, pneumatic dampers, hydraulic dampers or combinations thereof. In other forms, the counterforce is implemented as a shock absorber which slows down the movement between the cartridge and the needle unit immediately before the state of impact.

In one form the injection device includes an actuator in the form of an energy source coupled to the piston driver and configured for driving the piston driver upon release of the holding mechanism. The energy source may be provided as a stored energy source, such as a pre-strained spring, a compressed gas etc. In other forms, the energy source is configured to become charged during an initial operation of the device prior to activation of the injection mechanism. In still other embodiments, the actuator may be provided as a device which is manually driveable by the user of the device.

According to one embodiment the damping mechanism only exerts a counterforce during the movement of the cartridge before the expelling operation is initiated, thus allowing the full force of the spring to be used for ejecting the medicament once the cartridge and needle are connected. For example, the damping mechanism may be adapted to limit the speed of movement of the piston driver and hence the cartridge relative to the needle unit and to release the damping effect on the piston driver prior to the cartridge stops its movement relative to the needle unit.

For the various embodiments discussed above in relation to the second aspect of the invention, any of the combination of features noted above in relation to the first aspect of the invention may be combined to provide additional beneficial properties.

According to a third aspect of the invention, an injection device is provided comprising: a) a housing, b) a medicament cartridge having an outlet connected or connectable to a needle cannula and having a slideably arranged piston which is driveable towards the outlet, the medicament cartridge being adapted for movement relative to the housing, c) a piston driver capable of driving the piston towards the outlet of the cartridge, the movement of the piston driver relative to the housing defining a stroke length, d) an indicator capable of generating at least one of an audible, a tactile and a visible signal when the piston driver has travelled substantially the complete distance of said stroke length, the indicator having a deflection element which is at least partially deflected to accumulate energy during operation of the injection device and which is released to generate said at least one of an audible, a tactile and a visible signal, e) an actuator providing a stored energy source capable of being released to move the cartridge from a first position to a second position relative to the housing, to drive the piston driver and to deflect the deflection element, and f) an activator which upon operation releases said actuator. According to the third aspect the deflection element is configured for being at least partially deflected to accumulate energy prior to or during movement of the cartridge relative to the housing.

In accordance with said third aspect, a device is provided wherein an end of dose indicator uses a feedback mechanism which will be tensioned in the first part of the operation of the piston driver where the magnitude of the spring force is comparatively high. This means that more energy can be used for the feedback mechanism without sacrificing dosing force at times where the available spring force is most critical. Hence, a clear feedback may be provided communicating to the user when the injection is finished in order to prevent the user from removing the device from the injection site prematurely. Further, as an additional advantage, the tensioning of the feedback mechanism may limit or reduce the movement of the cartridge and in this way dampen the movement of the cartridge where this is desirable.

In one embodiment the injection device includes a cartridge of the type that comprises a cartridge septum sealing the outlet. Such device further comprises a needle cannula in the form of a needle unit having a front needle for penetrating the skin of a subject user and a rear needle for piercing the cartridge septum. The cartridge and the needle unit is configured for relative movement from a first state where the cartridge septum is sealed to a second state where the cartridge septum is pierced by the rear needle. Further the piston driver is adapted to cause the cartridge and needle unit to shift from the first state to the second state prior to driving the piston relative to the outlet of the cartridge. In such device, the deflection element is configured for being at least partially deflected to accumulate energy when the cartridge and the needle unit move relative to each other. Hence, in such an embodiment during connection of the needle unit and the cartridge the deflection element is used for minimizing the shock or impact which occurs during the connection operation where fluid communication is established between the contents of the cartridge and the needle. Also, dependent on the design of the mechanism, part of the stored energy can be used to drive the dosing at a later stage when the spring force is comparatively low. In addition a weaker spring can be used to drive the dosing mechanism.

In one form, the tensioning of a deflection element occurring during the first part of the expelling stroke provides for the full amount of the spring force being available during the remaining part of the expelling stroke.

In another embodiment wherein the cartridge outlet is connected to a needle cannula, the piston driver is adapted to move the cartridge from a first position to a second position to cause a tip end of the cannula to protrude from the device prior to the piston driver driving the piston towards the outlet of the cartridge. In such configuration the deflection element is configured for being at least partially deflected to accumulate energy during the cartridge movement from the first position to the second position. Hence, the deflection element is mainly or exclusively carried out during a needle penetration operation where the needle of the device is inserted into the skin. Hereby the tensioning of the deflection element is used for limiting the speed during which the needle pierces the skin of the user.

In the above described embodiments, the deflection element may be at least partly deflected by means of energy released from said stored energy source.

In further embodiments, after the deflection element enters into its fully deflected state and prior to the deflection element is released to generate said at least one of an audible, a tactile and a visible signal, the said accumulated energy of the deflection element may be gradually released whereby the deflection element may serve to assist in driving the piston driver by means of said gradual release of accumulated energy.

In still further embodiments the deflection element may be associated with one of the piston driver and the housing. A segmented surface profile may then be associated with the other of the piston driver and the housing. In such configuration, the segmented surface profile cooperates with the deflection element to provide for deflection of the deflection element to accumulate energy and to provide release of the deflection element to generate said at least one of an audible, a tactile and a visible signal.

As used herein, the term "medicament" is meant to encompass any medicament-containing flowable drug capable of being passed through a delivery means such as a hollow needle or cannula in a controlled manner, such as a liquid, solution, gel or fine suspension. Also lyophilized drugs which prior to administration are dissolved into a liquid form is encompassed by the above definition. Representative medicaments includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

DETAILED DESCRIPTION OF THE INVENTION

Figure 1B:
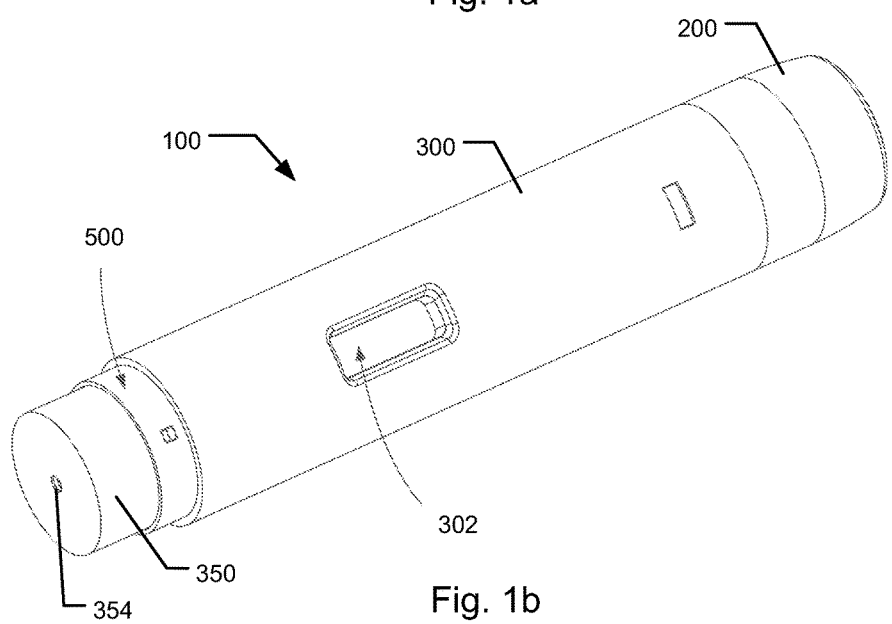
Figure 2A:
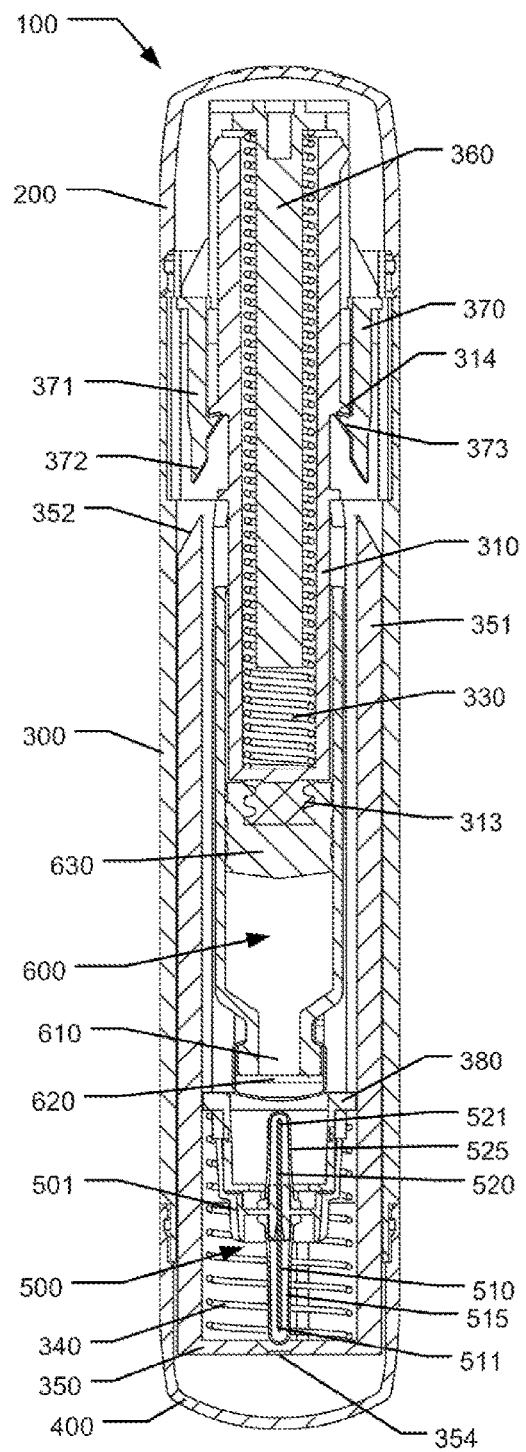
Figure 2B:
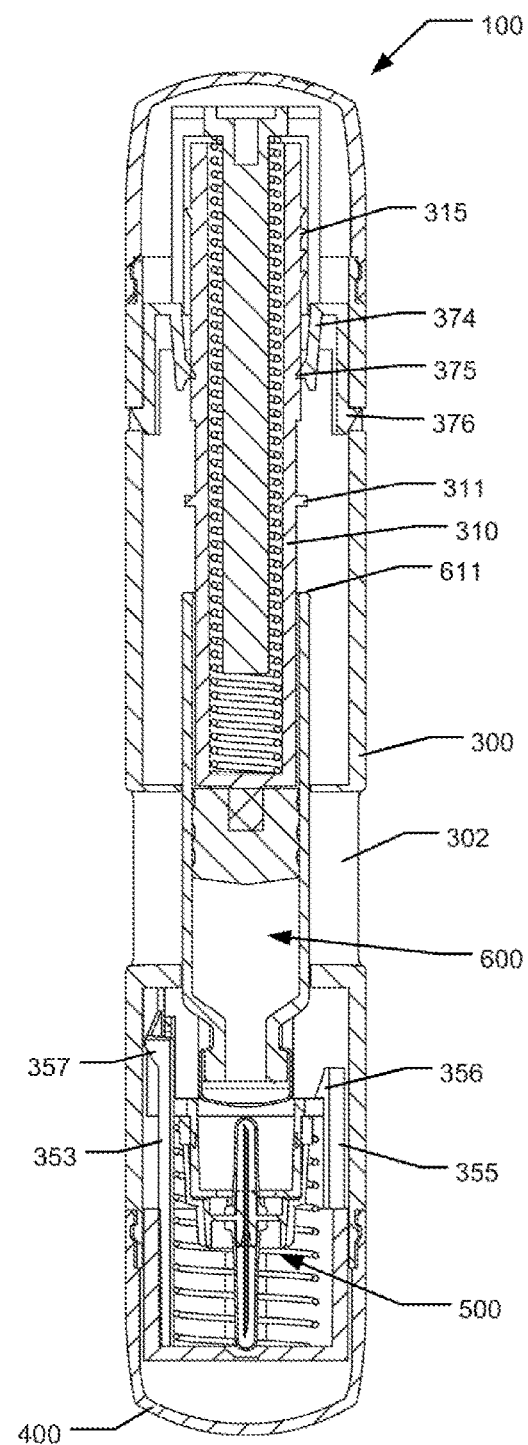
Figure 3A:
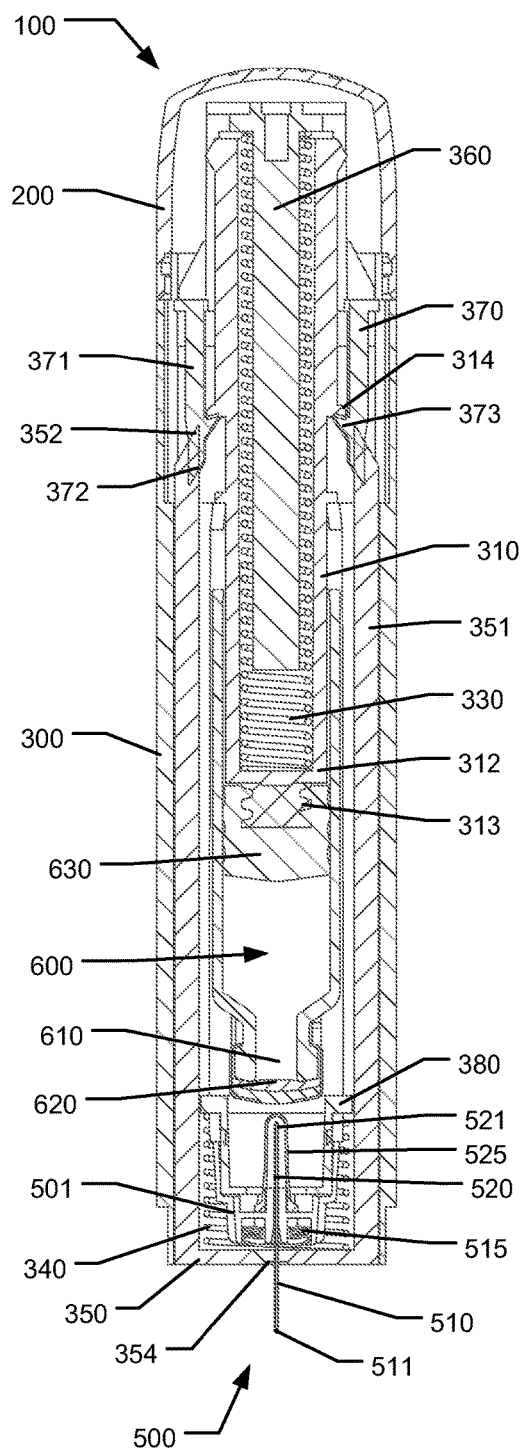
Figure 3B:
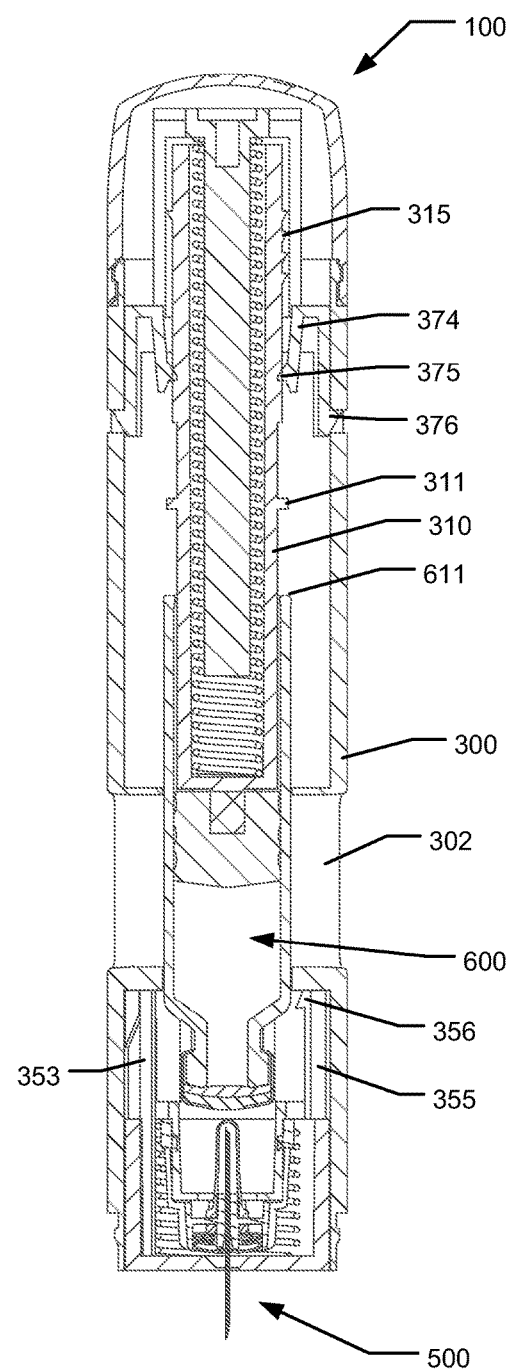
Figure 4A:
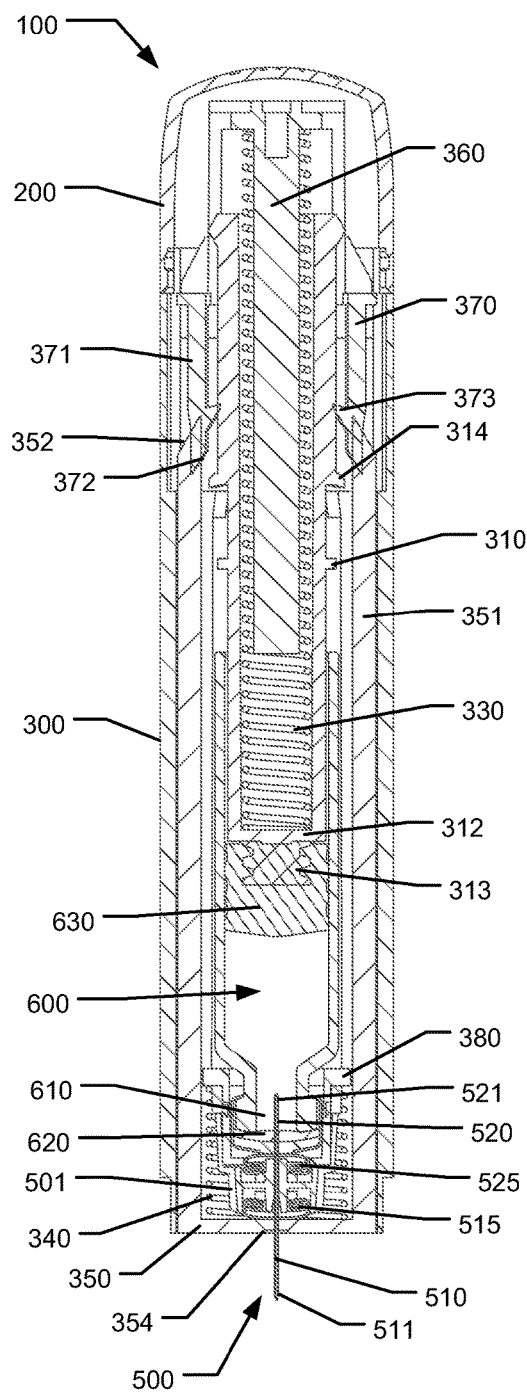
Figure 4B:
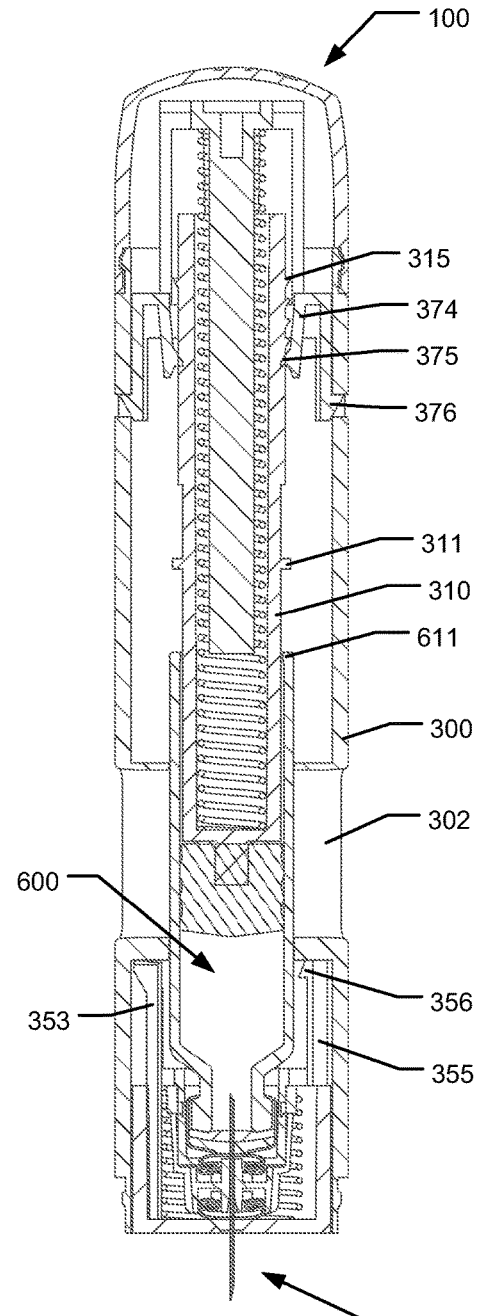
Figure 5A:
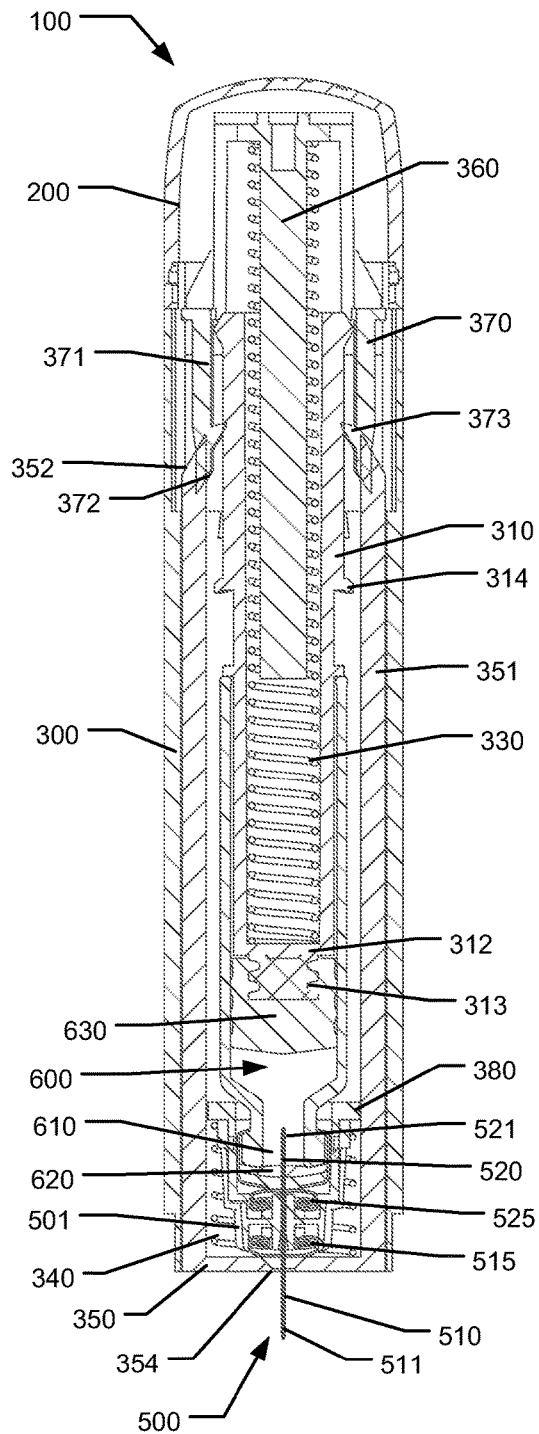
Figure 5B:
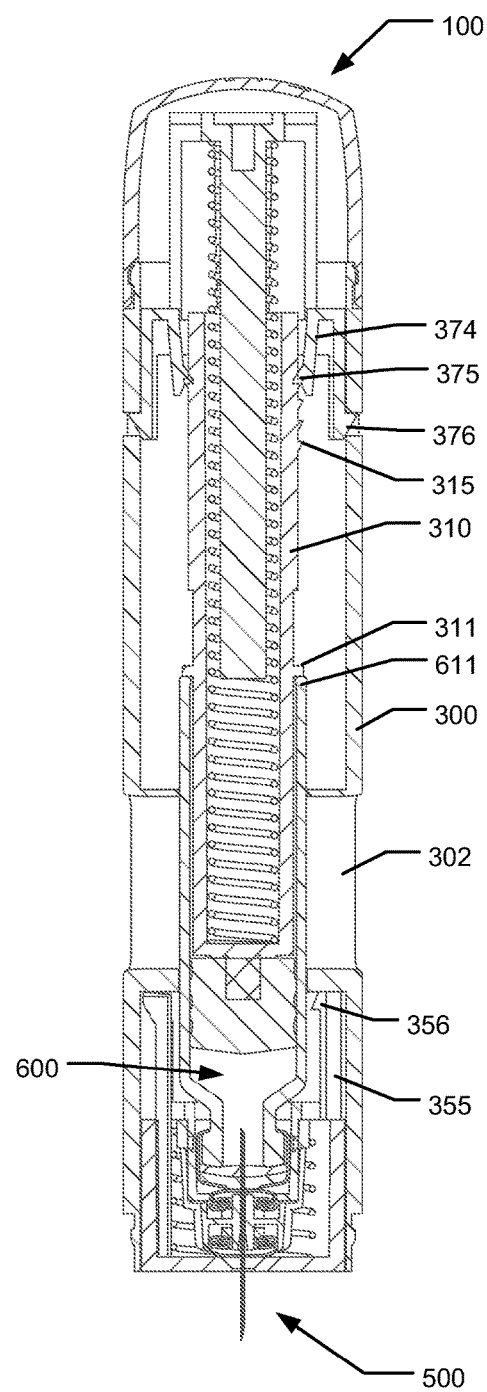
Figure 6A:
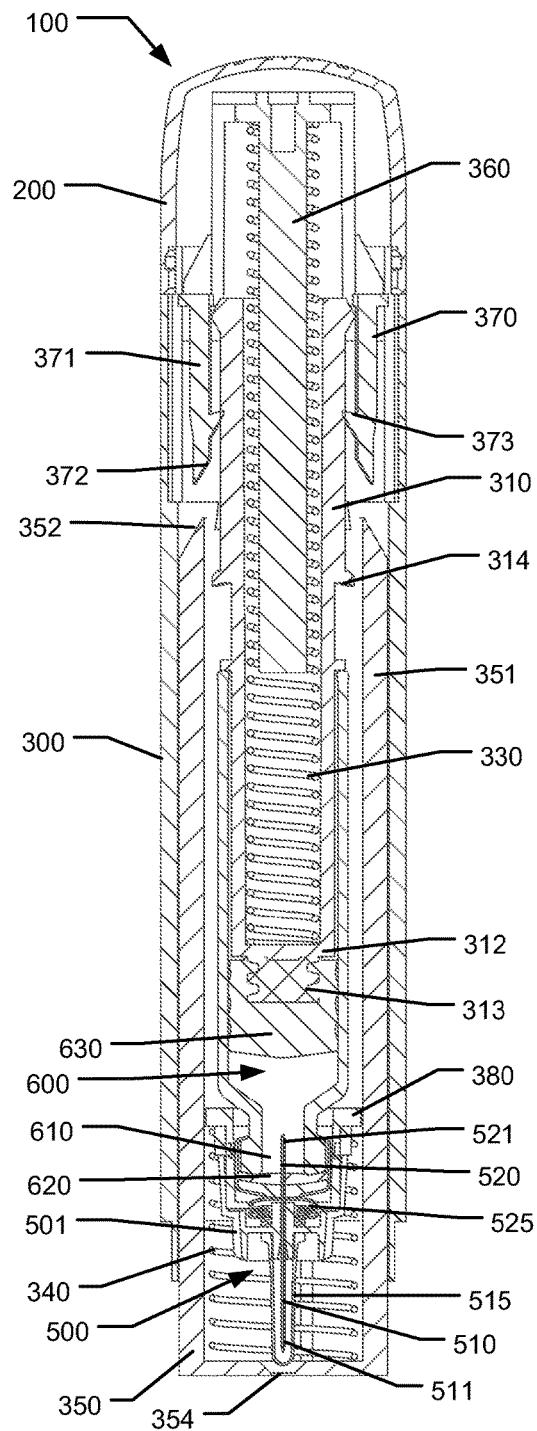
Figure 6B:
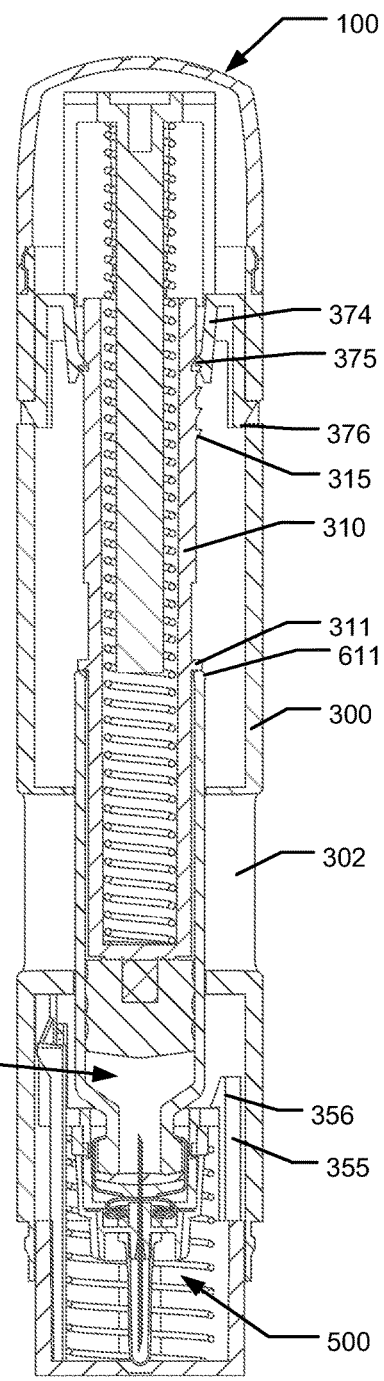

The invention will now be described in further detail with reference to the drawings in which:

FIGS. 1a and 1b are external perspective views of an injection device according to a first embodiment of the invention, FIGS. 2a and 2b shows front sectional views and side sectional views of the first embodiment illustrating a storage condition, FIGS. 3a and 3b shows front sectional views and side sectional views of the first embodiment illustrating a state where the front needle fully protrudes from the needle shield, FIGS. 4a and 4b shows front sectional views and side sectional views of the first embodiment illustrating a state where the cartridge connects to the needle for initial fluid delivery, FIG. 4c is a detailed view of the device illustrated in FIG. 4a showing elements of the retainer in its released state, FIGS. 5a and 5b shows front sectional views and side sectional views of the first embodiment illustrating a state at the end of dose condition, FIGS. 6a and 6b shows front sectional views and side sectional views of the first embodiment illustrating a shielded after use condition, FIG. 7 is a perspective detailed view of the needle shield of the first embodiment.

Figure 9A:
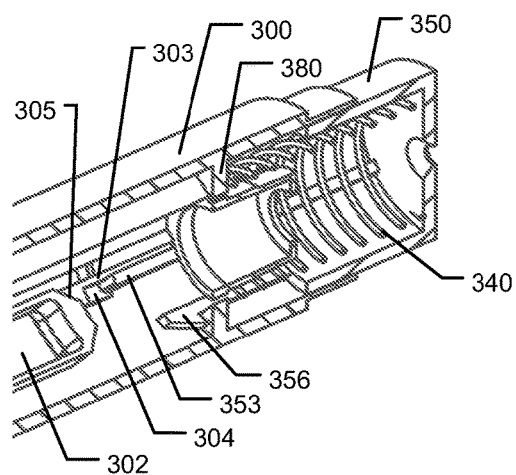
Figure 9B:
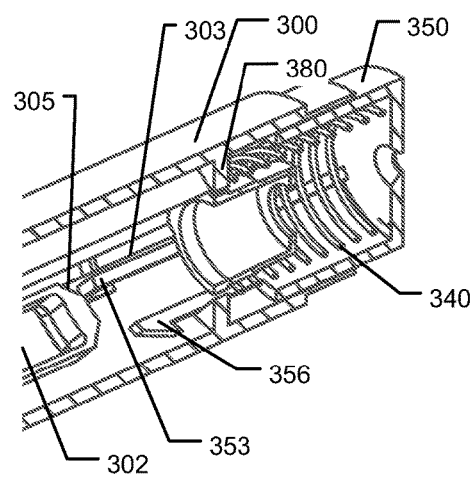
Figure 9C:
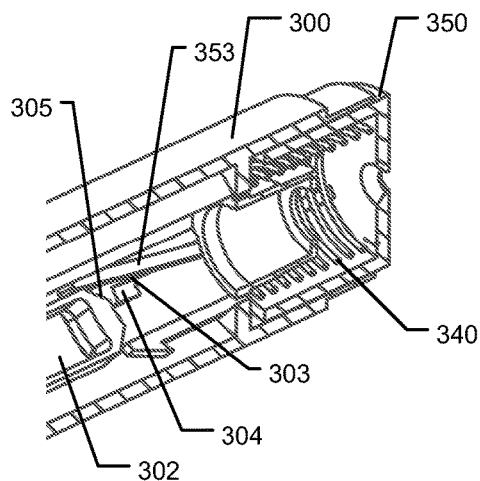
Figure 9D:
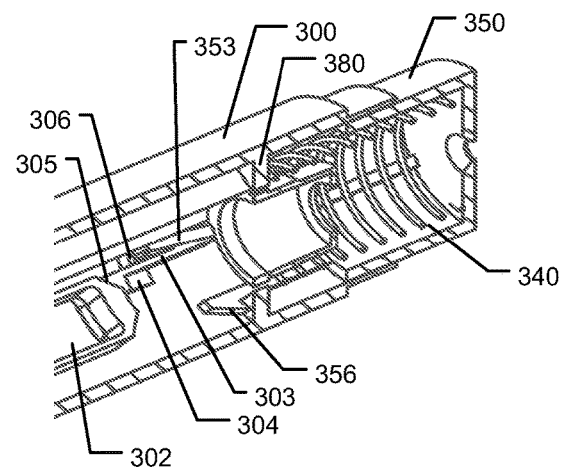
Figures 10A, 10B:
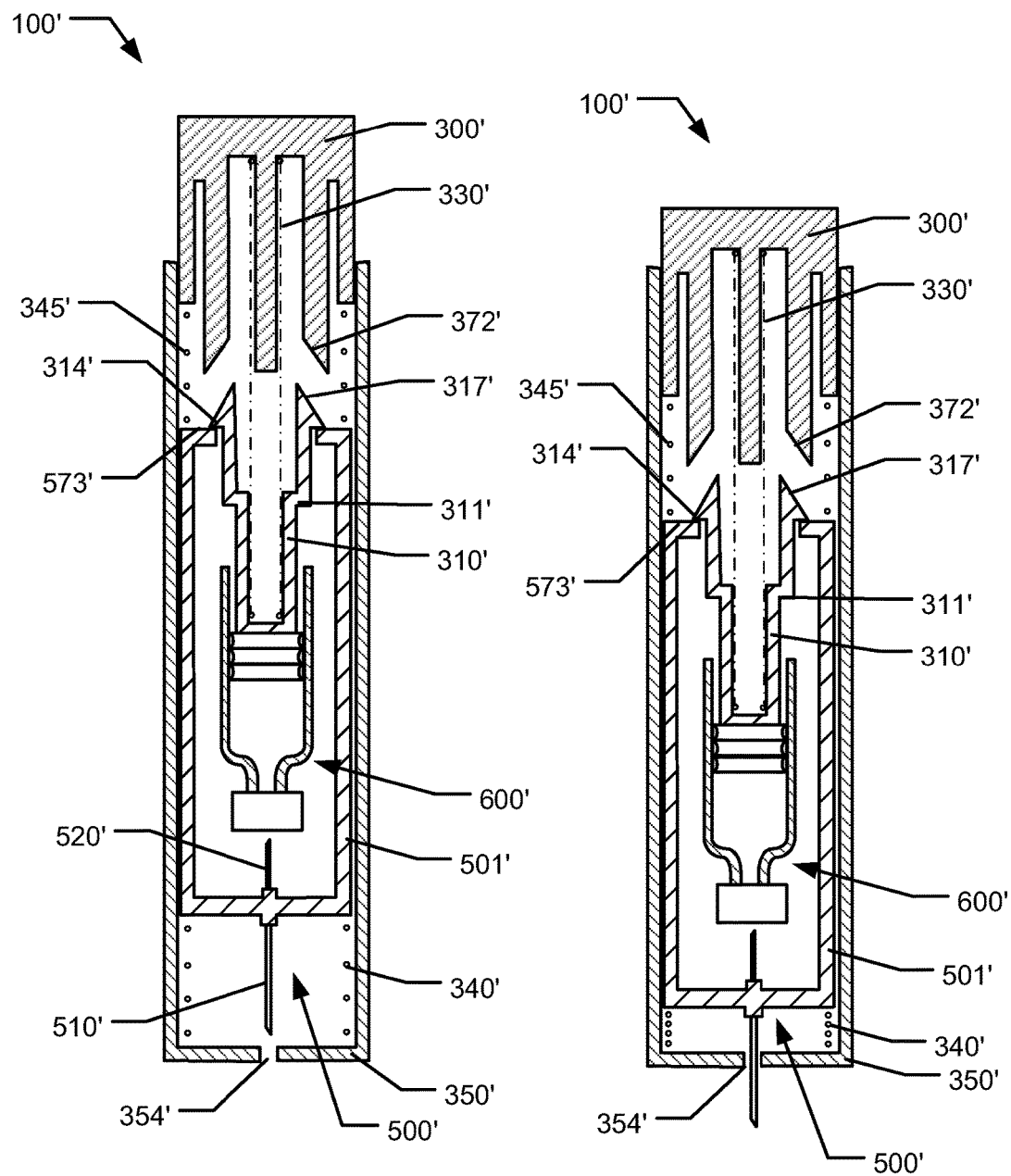
Figures 10C, 10D:
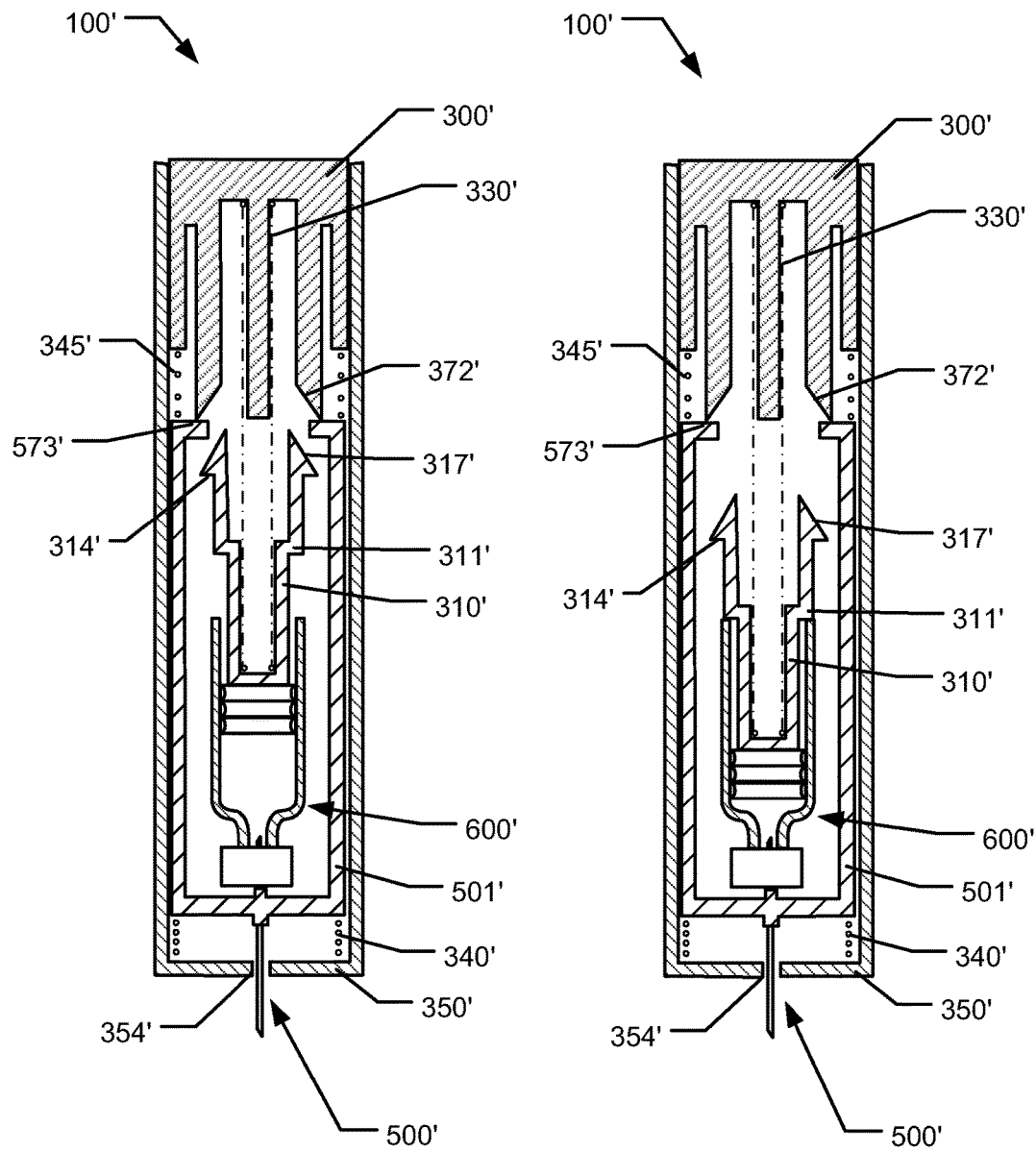
Figure 11C:
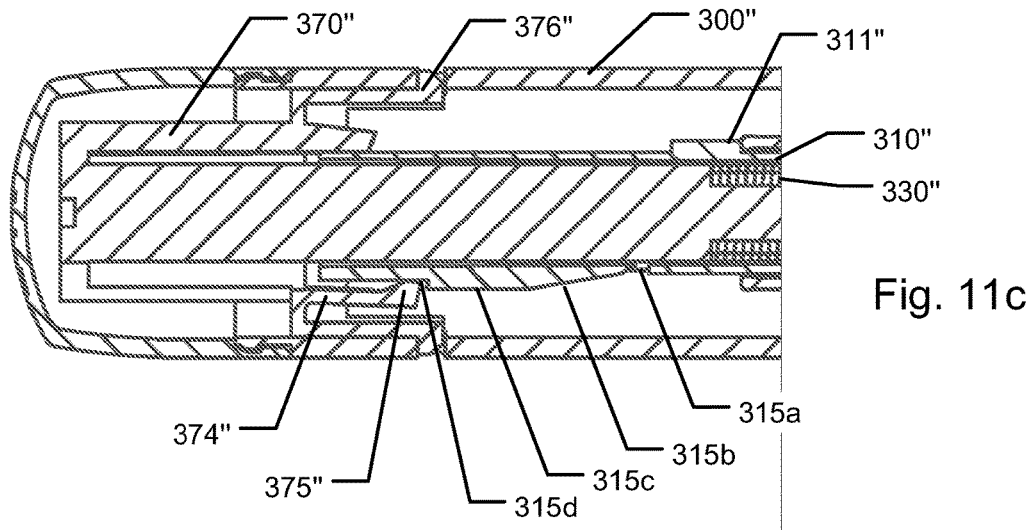
Figure 11B:
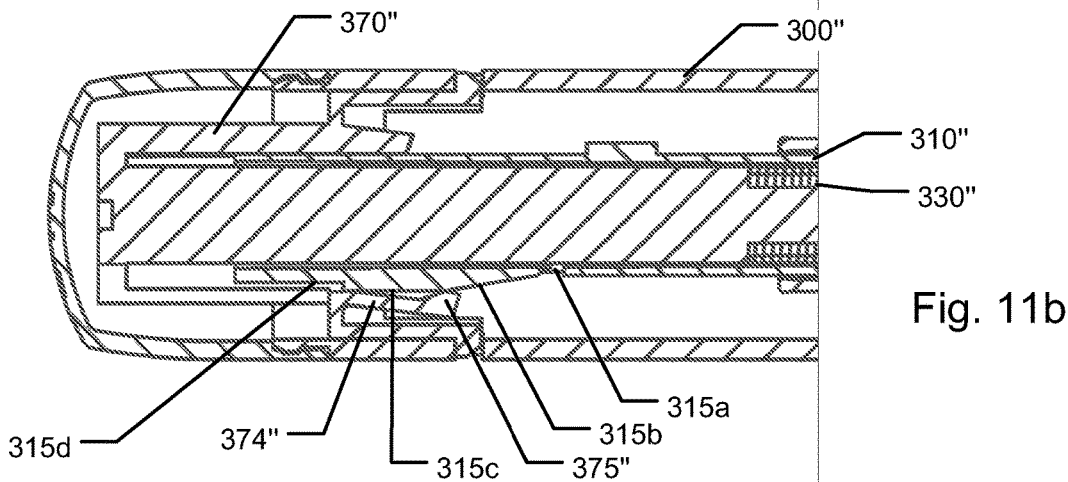
Figure 11A:
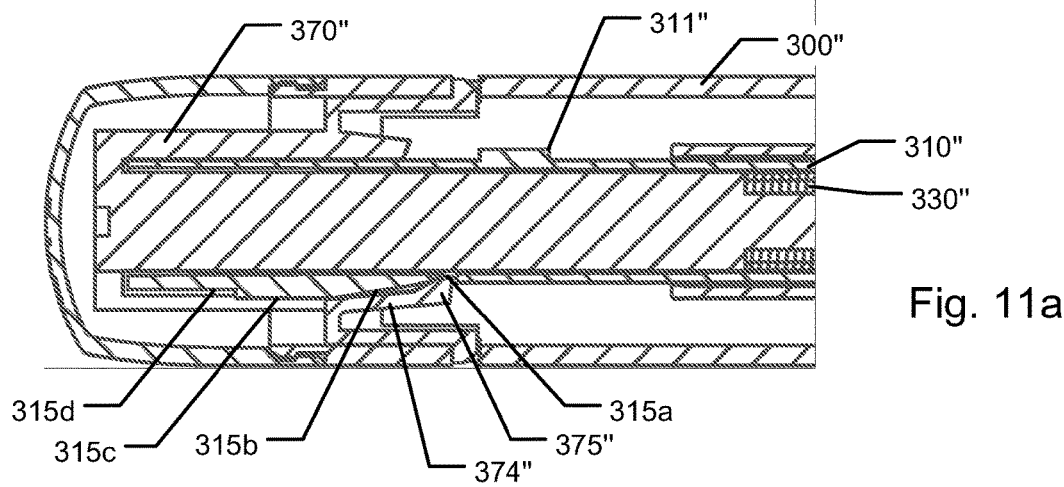
Figure 12A:
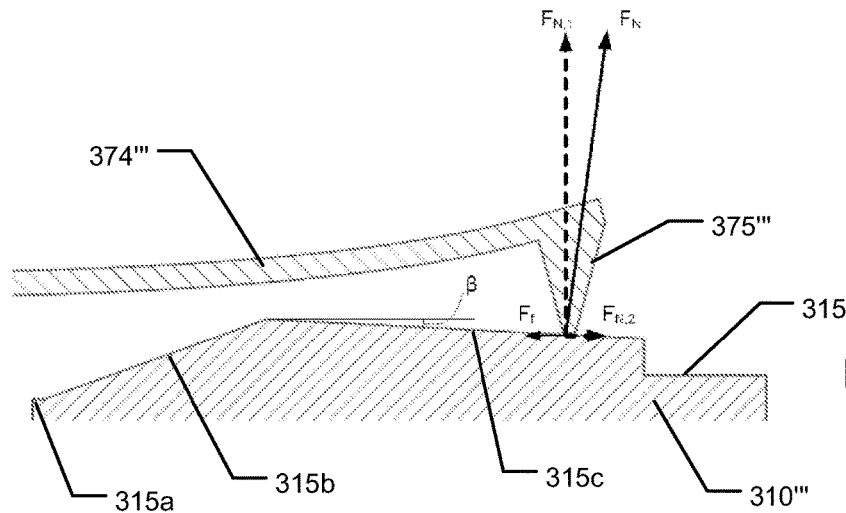
Figure 12B:
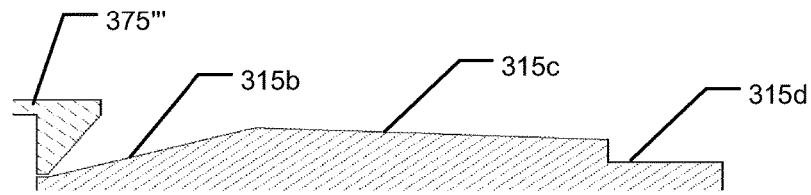
Figure 12C:
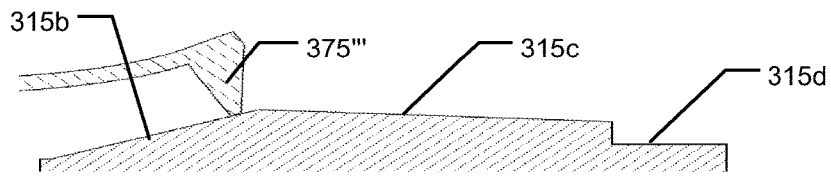
Figure 12D:
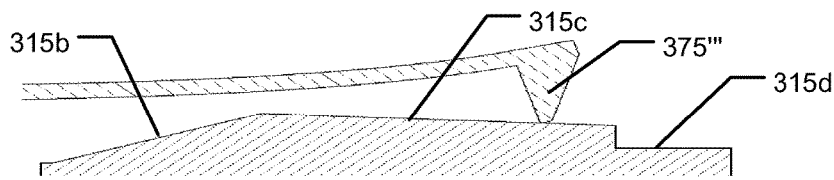
Figure 12E:
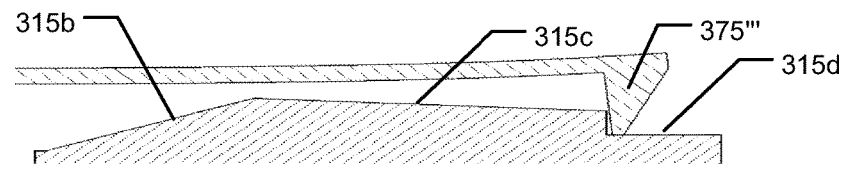
Figure 13A:
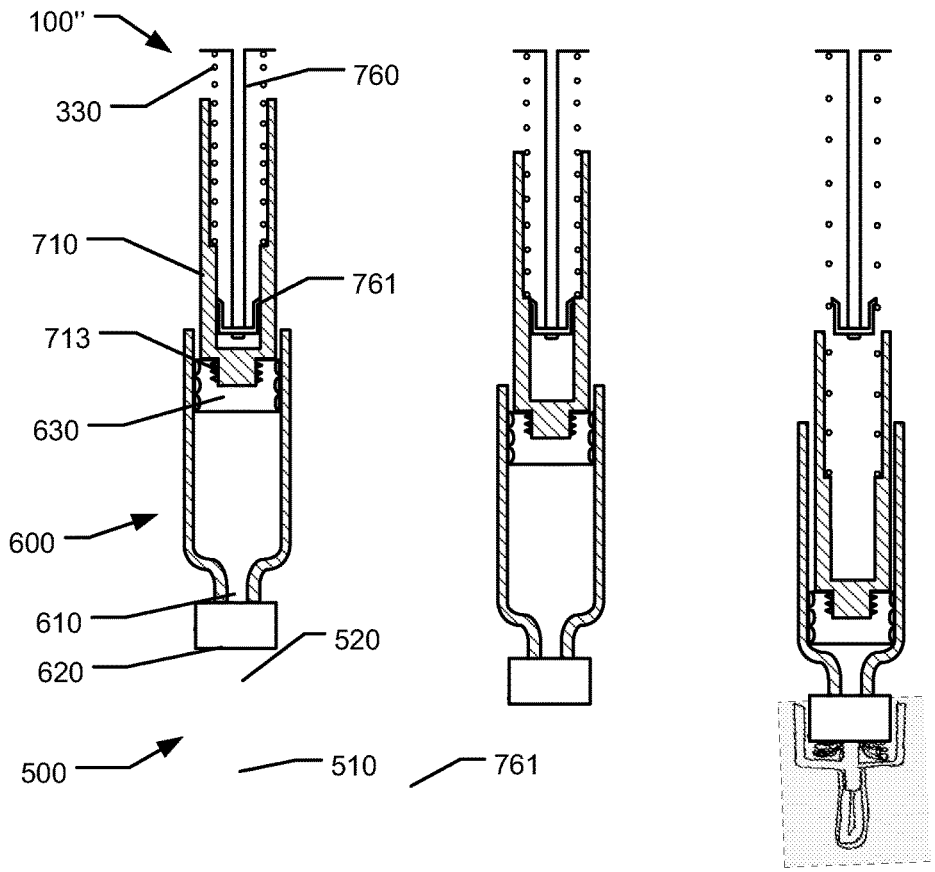
Figure 13B:
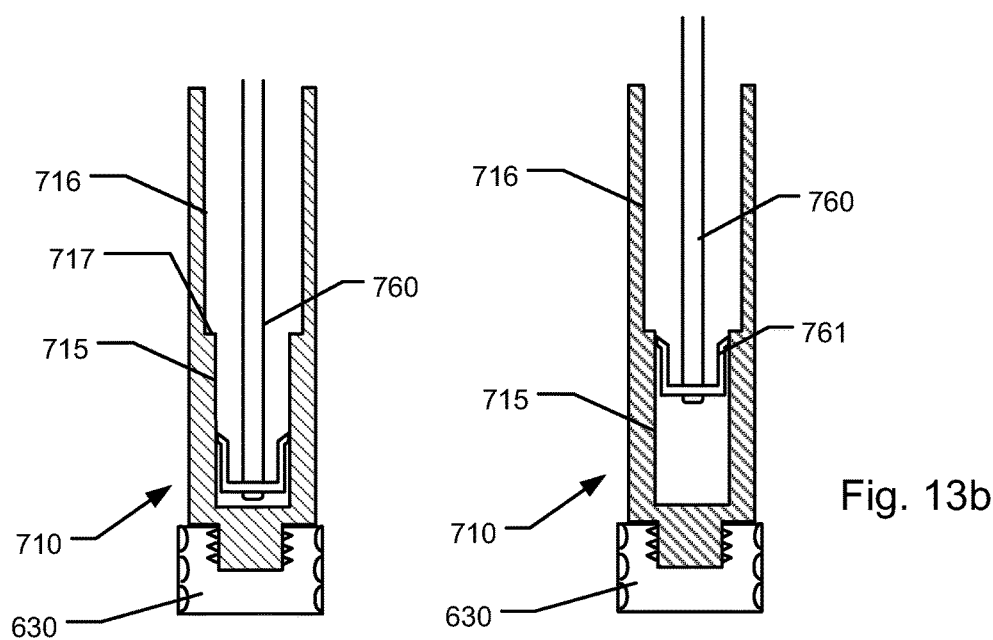

FIG. 8 is a perspective sectional view of the device of the first embodiment showing details of a needle shield lock mechanism, FIGS. 9a-9d show detailed sectional views of the needle shield lock mechanism in different states, FIGS. 10a, 10b, 10c and 10d respectively show sectional views of an injection device according to a second embodiment of the invention in an initial storage state, a needle protruding state, a state where the cartridge connects to the needle for initial fluid delivery and an end of dose state, FIGS. 11a-11c shows detailed sectional views of an end of dose confirmation indicator in different states according to a third embodiment, FIG. 12a-12e show schematic views of an end of dose confirmation indicator according to a fourth embodiment, FIG. 13a shows three schematic views of a fifth embodiment of an injection device which incorporates a damping mechanism, and FIG. 13b shows a more detailed view of the damping mechanism of FIG. 13a.

FIG. 1a shows a first embodiment of a medical injection device 100 for subcutaneously injecting a pre-determined amount of a liquid medicament. The injection device 100 includes generally tubular housing including a main housing section 300 and a top housing section 200 arranged at a proximal end of the device as well as a removable protective cap 400 arranged at a distal end of the device to protect a needle end of the device 100. The main housing section 300 includes two opposing windows 302 which allow visual inspection of the medicament contained within the device 100. In addition, the windows 302 allow a user of the device to determine whether or not the device 100 has been used for an injection. In the embodiment shown top housing section 200 is for manufacturing reasons formed as an element separate from but permanently fixed to main housing section 300 but may alternatively be formed integral with main housing section 300.

FIG. 1b shows the device 100 after the protective cap 400 has been removed but in a condition prior to use. Shown protruding from the distal end of the main housing section 300 is a needle shield 350 which is arranged coaxially and slideable relative to main housing section 300 between a distal extended position where a front end of a needle assembly 500 (not visible) arranged internally in housing 300 is in a shielded state and a second proximal compressed position where a front needle end of the needle assembly 500 protrudes through an aperture 354 arranged in the central part of needle shield 350.

The protective cap 400, when attached to the main housing section prevents the needle shield 350 from being manipulated and thereby prevents the activation of the injection device 100.

FIGS. 2a and 2b shows front and side sectional views of the injection device 100 shown in the state illustrated in FIG. 1a, i.e. with the protective cap 400 still attached to main housing section 300. Main housing section 300 accommodates a medicament filled cartridge 600 having an outlet 610 covered by a cartridge septum 620 adapted to be pierced by a needle for establishing fluid communication with the cartridge interior and having a slideably arranged piston 630. Piston 630 is driveable towards the outlet 610 when a needle pierces the cartridge septum 620 in order to dispense medicament from the cartridge 600. The dispensing is controlled by a dosing mechanism. Cartridge 600 is arranged movable with respect to the main housing section 300 from a proximal storage position to a distal position.

Distally in the main housing part 300 is a needle unit in the form of a needle assembly 500 arranged in an initially separated configuration with respect to cartridge 600. In the shown embodiment, needle assembly 500 includes a needle cannula having front needle 510 and rear needle 520 protruding in the distal and proximal directions respectively from a needle hub 501. Both front needle 510 and rear needle 520 include pointed tips 511 and 521 for respectively piercing the skin of a user and the cartridge septum 620.

Needle assembly 500 furthermore includes front 515 and rear covers 525 forming sterility sheaths of the front needle 510 and rear needle 520 respectively. In the shown embodiment, the front and rear covers are formed as rubber sheaths which are penetrable by the pointed tips 511 and 521 when the covers are forced towards the needle hub 501.

The needle cannula may be attached to the hub 501 by gluing, interference fit or similar joining process. The front 515 and rear cover 525 are attached to the hub 501 either by gluing, welding, interference fit, a separate mounting element, or similar. In the embodiment shown, the hub is a separate element which connects to main housing section 300 via a needle holder structure 380. Alternatively, the hub 501 may be designed to be part of another construction element in the device e.g. the hub could be part of a cartridge holder.

The needle assembly 500 is attached to the remainder of the device via an interface either on the device housing or on a cartridge holder. Prior to use the two covers 515, 525 are in their extended positions in which they cover the front 510 and rear needle 520 respectively.

In the shown embodiment, the needle shield 350 is formed as a tubular member having a distal face arranged to initially cover the front needle 510. Reference is made to FIG. 7 which shows the needle shield 350 in a perspective view.

The needle shield 350 is formed with a set of retaining arms 355, a set of locking arms 353, and a set of activation arms 351.

The needle shield 300 is mounted slidable relative to the main housing section 300 a preset distance but not allowed to rotate relative to the main housing section 300. The needle shield 350 is held in place by a shield spring 340 biasing the needle shield 350 to a distal position and the retaining arms 355 formed with hooks 356 which limit the distal movement of the shield to a position in which the hooks 356 contact a surface within the main housing section 300. The proximal movement of the needle shield 350 is limited by the front edge of the housing and the activation surfaces of the device. The activating arms 351 include angled surfaces 352 which is adapted to cooperate with a retainer for the dosing mechanism (to be further explained below).

The needle shield 350 moves along its axis and is rotationally fixed by the activation arms 351 which also functions as bearing surfaces contacting surfaces inside the main housing section 300.

As the device 100 is pressed against the patient's skin the needle shield 350 is moved to its proximal position. As the device 100 is removed the needle shield will move distally due to the force from the shield spring 340. After an injection has been performed, as the needle shield 350 reaches its distal position again, it will be locked in this position to render the needle shield inoperable (to be further explained below).

The needle assembly 500 is attached to the distal end of the main housing section 300, such that the needle shield 350 completely covers the needle assembly when the shield is its extended position. When the needle shield 300 is in its compressed position (i.e. the proximal position), the front needle 510 protrudes through the aperture 354 of needle shield 350.

The cartridge 600 is held by means of a piston driver 310 which is attached to the piston 630 of cartridge 600. In the embodiment shown, the piston 630 defines an internal thread adapted to attach to an external thread 313 located on the distal end of the piston driver 310. The cartridge is held within the injector by the connection between the piston driver 310 and the piston 630. Other attachment means such as snap locks or bayonet locks may alternatively be used. Still, in alternative embodiments, the piston driver 310 may be formed as a unitary component with the cartridge piston 630. As the piston driver 310 moves within the injector the cartridge 600 is moved distally as it is not affected by other parts. When the cartridge 600 reaches positioning means of the needle assembly 500 it is stopped, after which the piston 630 begins moving inside the cartridge 600. The relative movement of the piston 630 and the cartridge 600 ejects the medicament from the cartridge.

The dosing mechanism is placed in the proximal part of the housing of the device. In the shown embodiment the dosing mechanism comprises a piston driver 310, an actuator in the form of a pre-stressed compression spring 330 and a retainer 370. The retainer 370 is fixedly attached relative to the main housing section 300 by means of snap arms 376.

Further, the retainer 370 has a set of small arms 374 and a set of large flexible arms 371. The large set of flexible arms has angled ends forming triggering surfaces 372 and protrusions 373 which interact with the ledges 314 on the piston driver 310 keeping the piston driver arrested in a first position prior to activation of the injector. The small set of arms 374 has minor protrusions 375. The piston driver 310 is furthermore hollow to allow the dose spring 330 to be positioned within the piston driver 310. A guiding element 360 arranged internally in compression spring 330 may assist in guiding the compression spring 330 to prevent it from bending sideways.

The piston driver 310 is formed with stop surfaces 311 positioned a predetermined distance from the distal end of piston driver to cooperate with the rear end 611 of the cartridge 600 to thereby define a precise end of stroke position for the piston 630 inside cartridge 600. As the piston 630, during filling of the cartridge 600, may be accurately positioned with respect to the rear end 611 of the cartridge 600, the exact volume of an expelled dose can be accurately controlled by utilizing the stop surfaces 311 hitting the rear end 611 of cartridge 600 at completion of the expelling operation.

As mentioned, in the shown embodiment the actuator in the form of a pre-stressed compression spring 330 urges the piston driver in the distal direction. In the unactivated state of the injection device 100, retaining ledges 314 formed on an external face of the piston driver 310 couples to a retainer of the dosing mechanism for retaining the piston driver with respect to the main housing section 300 until activation of the dosing mechanism.

Alternatively to using a pre-stressed spring which is compressed during manufacture of the device, the device may include a mechanism for compressing the spring as an initial procedure when taking the device into use. Also, the actuator may in other embodiments be formed as a torsion spring which is pre-stressed to exert a torsion force for driving forward a rotational drive of the dosing mechanism. Alternatively, the actuator may be in the form of a compressed medium such as a gas. Still alternatively, the actuator may include a gas generator such as an electro-chemical cell.

Piston driver 310 further may include means (non-referenced) arranged at its proximal end to prevent the piston driver 310, when the device is in its storage condition, to move in the proximal direction. In the embodiment shown, piston driver 310 further includes one or more protrusions 315 adapted to cooperate with click arms 374 to generate click sounds during and/or at the completion of the injection.

As mentioned previously, the activation surfaces 352 of the needle shield 350 are positioned on activation arms 351 protruding from the needle shield 350. As the needle shield is moved in the proximal direction the activation arms 351 moves towards the triggering surfaces 372 of the flexible arms 371 on the retainer 370. As the activation surfaces 352 contact the triggering surfaces 372 and are moved further, the higher stiffness of the activation arms 351 and the incline of the triggering surfaces 372 and activation surfaces 352 will cause the flexible arms 371 of the retainer 370 element to bend radially outwards. As the flexible arms 371 bend outwards, the retaining surfaces 373 are moved sideways across the retaining ledges 314. As the retaining surfaces 373 are moved completely away from the retaining ledges 314 the piston driver 310 is released for movement (refer to FIG. 4c).

In the following, while mainly referring to FIGS. 2a through 6b, operation of the injection device will be described.

As mentioned above FIGS. 2a and 2b shows the device in its initial storage condition with the protective cap 400 attached to the main housing section 300. The needle shield 350 is in its extended position whereby the front needle is in a shielded state.

Before use, the protective cap 400 is detached. In accordance with the above description, the main housing section 300 acts as an activator relative to the needle shield 350, in that as the main housing 300 is gripped by the hand of the user and the distal end of device 100 is pressed against an injection site the needle shield 350 will remain arrested relative to the skin and the main housing moves distally relative to the needle shield 350 for activating the dosing mechanism of the device 100.

As the device 100 is activated the needle shield 350 is moved in a proximal direction relative to main housing section 300 towards the needle assembly 500. The movement brings the front needle 510 through the small aperture 354 in the needle shield 350. As the needle cannula moves relative to the aperture 354 the front cover 515 is preferably held back by the geometry around the opening, thereby allowing the front needle 510 to penetrate the front cover 515 while the needle cover 515 is being compressed between the needle shield 350 and the needle hub 501. Alternatively the front cover 515 could move through the aperture 354 as well. In this case the front cover 515 would be pressed against the patient's skin, thereby being compressed between device 100 and skin. The compression of the front cover 515 can be either in a concertina-like way or be bent sideways, e.g. radially outwards. The front cover 515 may have a specific geometry to ensure that the front cover 515 is always compressed between needle shield 350 and needle hub 501. The aperture 354 in the needle shield 350 could also have a specific geometry for ensuring correct compression of the front cover 515. As the needle shield 350 reaches a predetermined position the needle shield 350 will reach a stop. In this position the front needle will be inserted in the patient's skin and the front cover will be compressed. This state is depicted in FIGS. 3a and 3b where the needle shield is pushed fully in the proximal direction and where the activating surfaces 352 reach sufficiently proximally to engage the triggering surfaces 372 of retainer 370 to release the retainer for piston driver 310 release. Note however, that in FIGS. 3a, 4a and 5a, the activating arms 351 including the activating surfaces 352 are shown superposed relative to the cooperating flexible arms 371 with triggering surfaces 372 to schematically illustrate the engagement. A more correct depiction of how the flexible arms 371 of retainer 370 deflect during this engagement is shown in FIG. 4c.

After the movement of the needle shield 310 has reached its stop, the cartridge 600 will move distally relative to main housing section 300 and needle assembly 500. This movement will cause the septum 620 to contact the rear cover 525, thereby compressing this. The compression of the rear cover 525 will cause the rear needle to penetrate through the rear cover 525 and septum 620 of cartridge 600. The compression of the rear cover 525 can be either in a concertina-like way or be bent sideways. The cartridge 600 is further moved until a predetermined position in which the movement is stopped. This condition of the device 100 where the activation arms 351 of the needle shield 350 has activated the device but where fluid delivery has not yet commenced, is shown in FIGS. 4a 4b and 4c. The compression of the rear cover 525 could act as dampening for the movement of the cartridge 600, thereby reducing the mechanical impact as the cartridge 600 is stopped. In this position the rear cover 525 is compressed between the hub 501 of the needle assembly 500 and the front end of the cartridge 600. The needle cannula is in this position in contact with both the patient's skin and the medicament contained in the cartridge.

After fluid communication between needle cannula and cartridge 600 is established the medicament is injected into the patient by means of the piston driver 310 being now released relative to retainer 370 and being urged distally by actuator 330. As the cartridge 600 moves forward the distance between the stop surfaces 311 and the rear end 611 of the cartridge 600 remains unchanged as the piston 630 does not move relative to the body of the cartridge 600. However, after the cartridge 600 has been moved fully in the distal direction, as the piston 630 begin its movement inside cartridge 600 the distance decreases. When the stop surfaces 311 of piston driver 310 reaches the rear end 611 of the cartridge 600 the movement of the piston driver 310 is stopped, thereby stopping the dosing of the medicament. This state of the device is shown in FIGS. 5a and 5b.

As depicted in FIGS. 6a and 6b, after injection the device 100 is removed from the skin of the user. As the device is removed the needle shield 350 is moved forward relative to the main housing section 300, thereby releasing the compressive pressure on the front cover 515. As the needle shield 350 no longer holds the front cover 515 in a compressed position the front cover will tend to return to its extended position covering the front needle 510. In alternative embodiments, the front cover 515 may be so configured as to return the front cover 515 to its uncompressed shape which could act as a spring biasing the needle shield 350 to return to its distal position. Such configuration would obviate the need for a dedicated shield spring. Still, alternatively the front cover 515 could remain in its compressed position.

As the device 100 is removed from the patient the front needle 510 is removed from the skin of the patient. If the front cover 515 returns to its extended position the front cover will prevent excess medicament expelled from the needle cannula to drip out from the device. The rear cover 525 remains in its compressed position due to the pressure from the cartridge 600.

As mentioned above the needle shield 350 may include a lock which renders the needle shield 350 locked against proximal movements once it has been returned from a proximal position to the most distal position, i.e. where the front needle 510 is in its shielded state. In the depicted embodiment however, the lock function of the needle shield 350 is only activated once the needle shield 350 has been pushed in the proximal direction past a predetermined lock activation position. The predetermined lock activation position may be arranged distally but closely to the position where the locking arms 351 of the needle shield 350 has fully triggered the retainer 370 for piston driver 310 release. For needle shield movements less than the said predetermined lock activation position, the front needle may protrude sufficiently far from the needle shield to allow a partial needle insertion into the skin. Hence, when the needle shield 350 is moved proximally but not quite reaching the said predetermined lock activation position and the needle shield 350 is returned to its most distal position, the said lock will not be activated and the needle shield may be moved proximally again for attempting to use the injection device 100 for a successful administration.

In the shown embodiment, and as shown in detail in FIGS. 7, 8 and 9a through 9d, the shield lock is caused by the locking arms 353 each having a proximal part 357 formed as track follower to cooperate with respective cams formed internally in the main housing section 300. As the shield 350 is moved proximally the locking arms 353 (and the track followers 357) each follow a path along the inside of the housing until they reach a set of angled surfaces 304 (see FIG. 9a) which forces the locking arms 353 away from the housing wall and radially inwards into the position shown in FIG. 9b. Further proximal movement of the needle shield 350 causes each of the locking arms 353 to abut an inclined wall section 305 whereby the locking arms 353 are forced sideways. As the arms are bent sideways they are moved to a groove positioned next to the path as shown in FIG. 9c. The path and the groove are separated by a ridge 303 preventing the locking arms 353 form returning to their initial state. As the device 100 is removed from the patient's skin the needle shield 350 will move distally due to the shield spring 340. The movement will cause the locking arms 353 to move along the groove and past a smaller ridge 306 placed across the groove. The smaller ridge 306 has a geometry which allows the locking arms 353 to move past it from one direction only. As the needle shield 350 reaches its most distal position the proximal part 357 of the locking arms 353 abuts the forward surface of the smaller ridge 306, thus preventing the needle shield 350 from being moved proximally thereby locking the needle shield in place. Hence, after the device has been used for performing an administration, accidental needle sticks are prevented.

Now turning to a second embodiment of an injection device 100' of the invention, FIGS. 10a through 10d shows a device which includes a needle shield 350' which is of generally tubular shape and which additionally performs as a housing section for at least partly accommodating a medicament cartridge 600' and a needle unit in the form of a needle assembly 500'. In use, the needle shield 350' is grippable by the hand of a user for positioning the device at an injection site. A distal face of the needle shield 350' includes an aperture 354' through which the front needle of the needle assembly 500' may be moved to extend beyond the needle shield 350'. In the proximal end of needle shield

350', an activator in the form of an injection button 300' is arranged for activating the device.

The said needle assembly 500' may be generally formed similar to the needle assembly 500 of the first embodiment. However, the needle assembly 500' in the shown second embodiment includes a hub section which extends towards the proximal portion of a piston driver 310' and includes a retainer section having retaining surfaces 573' which is used for retaining piston driver 310' relatively to the needle assembly 500' until activation of the injection.

In the storage condition, the piston driver 310' is urged in the distal direction due to an actuator in the form of a pre-stressed compression spring 330'. As in the first embodiment, the cartridge 600' is held stationary relative to the needle assembly 500' by means of the piston driver 310' which is attached to the piston of the cartridge 600'. Cartridge 600' moves in unison with the needle assembly until the retainer is released for relative movements between cartridge 600' and needle assembly 500'.

A shield spring 340' is arranged between the needle shield 350' and the needle assembly 500' so that the needle assembly 500' may be pressed in the distal direction for the front needle of the needle assembly 500' to extend beyond the needle shield 350'. The activation button 300' connects to the needle assembly 500' by means of an activator spring 345' having a larger spring constant than the shield spring 340'. Hence, upon activation of the button 300' to press it in the distal direction, manual force is transferred by means of the activator spring 345' to move the needle assembly 500' in the distal direction. This penetrates the front needle into the skin of the patient.

The activation button 300' further includes activation arms each having an inclined surface 372' which engages mating triggering surfaces 317' arranged in the proximal end of the piston driver 310'. After the needle has penetrated into the skin, by applying continued pressure on the activation button 300', the inclined surfaces 372' will move the triggering surfaces 317' radially inwards, as the activation spring 345' is compressed. When the triggering surfaces are forced radially inwards, retaining ledges 314' of the piston driver 310' are released from the retaining surfaces 573' of the needle assembly 500'. Hence, as the spring 330' forces the piston driver 310' distally, the cartridge 600' moves distally until a rear needle of the needle assembly 500' penetrates the septum of the cartridge 600' to establish fluid communication between the cartridge interior and the needle cannula. This fluid communication allows for continued movement of the piston driver 310' which thereafter plunges forward the piston of the cartridge. This movement is maintained until a stop surface 311' of piston driver 310' abuts the rear of the cartridge which completes the expelling operation. As in the first embodiment, an end of dose indication by means of an audible or tactile click sound may be generated to signal when the expelling operation is completed.

Hereafter, the pressure exerted upon activator button 300' may be released, which allows the shield spring 340' to expand to withdraw the needle assembly 500' in the proximal direction so as to withdraw the front needle from the needle shield 350'. Hereafter, the injector may be safely discarded. It is noted that safety features discussed in relation to the device 100 of the first embodiment, such as a needle shield lock which renders the front needle to be locked in its shielded state after use may be incorporated in the device 100' according to the second embodiment.

In accordance with the above description, FIGS. 10*a*, 10*b*, 10*c* and 10*d* respectively show sectional views of the injection device 100' according to the second embodiment where FIG. 10*a* shows the device in an initial storage state, FIG. 10*b* shows the device where the front needle of the needle assembly 500' has been brought into the unshielded state by pressing on activator button 300', FIG. 10*c* shows the device in a state after the cartridge 600' has been released for movement relative the needle assembly 500' and where the needle connects to the cartridge interior at the initial stage of fluid delivery, and FIG. 10*d* shows the device in the end of dose state after completion of the injection stroke.

In accordance with a third embodiment which is shown in FIGS. 11*a* through 11*c*, an improved end of dose confirmation indicator for an injection device is disclosed. The end of dose confirmation indicator provides an audible and/or tactile signal at the end of stroke position for signalling when the dose expelling operation has been completely fulfilled, i.e. the condition where the remaining few droplets that usually drips from the needle after the end of stroke condition is considered negligible.

The details of the drawings relate to an embodiment that substantially corresponds to the first embodiment but with the following modifications. The end of dose indicator again comprises a retainer 370" having a flexible arm 374" with a protrusion 375" that is adapted to cooperate with surface features of the piston driver 310". In addition, the retainer 370" is formed integral with a guiding element arranged internally in the compression spring 330" of the device. In the shown embodiment, the injection device is configured to remain substantially silent during the course of the expelling operation but with a significant end of dose confirmation click being generated a fraction of time before the end of stroke condition where the stop surface 311" abuts the rear of the cartridge (see FIG. 11*c*).

Referring to FIGS. 11*a*-11*c*, the end of dose indicator consist of a deflection element in form of one or more flexible arms 374" placed on the retainer 370" which each cooperates with a segmented protrusion on the piston driver 310". The segmented protrusion on the piston driver 310" forms a segmented surface profile which has a first part formed as a small angle incline 315*b*, a second part formed as a straight surface 315*c* and a third part formed as drop-off to a surface 315*d* placed relatively lower than the middle part. Immediately before the first part of the protrusion is a cut-out 315*a* in the piston driver 310". Prior to use the flexible arm 374" of the retainer 370" rests in the cut-out 315*a* to prevent tensioning the arm during storage to avoid creep of the material. During the dosing of the medicament, the piston driver 310" will move relative to the retainer 370", thereby moving the flexible arm from the cut-out 315*a* across the three parts of the segmented surface profile. As the flexible arm 374" moves across the incline 315*b* the arm is brought into a tensioned position. This position is held as the arm moves across the second part 315*c*. As the flexible arm 374" moves past the drop-off the tension of the arm will cause it to accelerate towards the surface of the last part 315*d* of the segmented surface profile, impacting the surface and producing an audible feedback to the user. In alternative embodiments, the movement of the flexible arm 374" may alternatively or in addition serve as an indicator providing a tactile indication to the user, a visible indication or both.

The edges included at the protrusion 375" of the flexible arm 374" and the drop-off leading to the surface 315*d* are inclined to ensure that no surfaces of the two parts impact each other prior to the intended impact, which otherwise would result in braking the flexible arm and reducing the emitted indication.

In the third embodiment, the incline 315b" is arranged along the piston driver 310" so that the flexible arm 374" will be tensioned during the movement where the piston driver 310" advances the cartridge in the distal direction relative to the needle assembly but before the advancement of the cartridge stops. In the latter position the piston driver 310" commences to drive the piston relative to the body of the cartridge whereby a comparatively high spring force of the actuator is required to overcome the static friction between the piston and the internal walls of the cartridge as well as the force needed to expel the medicament through the needle cannula. During these states the segmented surface profile may even comprise segments having a negative incline so that the accumulated energy of the deflection element is gradually released to thereby assist the actuator, i.e. the spring 330" in driving the piston relative to the outlet of the cartridge by means of said gradual release of accumulated energy.

Such configuration is shown in FIG. 12a which shows a piston driver 310''' having a segmented surface profile and a deflection element 374''' according to a fourth embodiment.

FIGS. 12b through 12e show the process of tensioning and releasing the feedback mechanism. A deflection element including protrusion 375''' is positioned in an initial position when the device is not yet activated. As the device is activated the cartridge is moved towards the needle assembly. During this movement the deflection element will be pressed against the first incline of the piston driver 310''' (315b), thereby tensioning the deflection element. The tensioning of the deflection element will further act as a dampening mechanism for the movement of the cartridge, reducing the shock of the connection between needle and cartridge. When the cartridge is connected to the needle cannula the ejection of the medicament through the cannula begins. During this the deflection element moves along the second incline (315c) which is reversed compared to the first. As the deflection element moves along the incline it is affected by a frictional force working against the movement. The reverse incline results in contact forces which will counteract the frictional forces (as seen in FIG. 12a). The size of the contact force counteracting the frictional forces is dependant on the angle of the second incline, β. As the dosing is nearly completed the deflection element reaches the drop-off between the second incline 315c and the final plane 315d of the segmented surface profile. The last movement of the dosing mechanism brings the deflection element over the drop-off resulting in an impact between the deflection element and the final plane 315d, thus resulting in a clear audible indication that the dosing has finished.

In the above described third and fourth embodiments the segmented surface profile is placed on the piston driver and the deflection element is attached to the housing or an element positioned within the housing. It is understood that in other embodiments, the position can be reversed. Also, instead of using the piston driver for one of the elements of the feedback mechanism, any other component where movement is associated with movement of a piston driver may be utilized.

The angle, β, of the second incline can be designed according to the requirements of the contact force $F_{N,2}$, thereby changing the ratio between the frictional forces and the contact force. This can be used to design the force profile of the dosing as desired e.g. providing extra dosing force at the last part of the dosing where the spring force is lowest.

The improved end of dose confirmation indicator according to the third and fourth embodiments may alternatively be implemented as part of an injection device 100' according to the second embodiment or in any other injection device where the energy distribution during a stroke of an element is considered relevant. For example, in an injection device which includes a cartridge with a needle cannula fixedly attached to the cartridge body, the tensioning of a deflection element to thereby accumulate energy may be performed during a needle penetration procedure and optionally, or alternatively, during the first part only of the dose expelling stroke.

FIGS. 13a and 13b schematically show details of a fifth embodiment of an auto-injector 100" having a cartridge 600 and having a damping mechanism for limiting or slowing down the speed of the cartridge as it moves distally in the injector housing relative to the needle assembly 500 prior to the expelling procedure. The overall operating principle for the auto-injector of the fifth embodiment corresponds to the overall operating principle of the injection device 100 of the first embodiment but with the following modifications. In FIG. 13a, for clarity reasons, a large number of parts and details have been omitted from the drawings and therefore only components and details relevant to the operating principle of the damping mechanism are shown. The releasable holding mechanism that maintains the piston driver in an arrested state prior to activation of the device is omitted as well.

Referring to FIG. 13b, left view, the piston driver 710 is shown modified to include a first bore 715 and second bore 716 for accommodating further parts of a damping mechanism. An annular ridge 717 performs as a seat for the actuator spring 330. As in the first embodiment the piston driver 710 is initially held in place by a retainer. The piston driver 710 is furthermore attached to the medicament cartridge 600 by means of a threaded connection 713 between piston driver and cartridge piston 630. A top element 760 protrudes from the proximal end of the housing (not shown) and into the two bores 715 and 716 of the piston driver 710. The top element 760 is firmly attached to the housing at the proximal end whereas the distal end of the top element 760 is provided with a flexible element 761 which engages the inner bore 715 of the piston driver 710.

As the device is activated the piston driver 710 is released from the retainer allowing the piston driver 710 to move in the distal direction with the medicament cartridge 600 attached. This movement causes a septum part of the cartridge 600 to be connected to the rear needle of the needle assembly 500 (as shown in FIG. 13a, left and middle images). As the cartridge 600 is connected to the injection needle, it is prevented from moving further, whereby the piston 630 within the cartridge starts to move, thus initiating the injection of the medicament.

During the first part of the movement of the piston driver 710 and cartridge 600, the flexible element 761 attached to the top part 760 will be in contact with the inner walls of the first bore 715 of the piston driver 710 in a manner providing a sealing contact but having a well controlled leaking effect as the piston driver 710 moves relatively to top part 760. As the piston driver 710 moves distally, the contact between the flexible element 761 and the walls of the first bore 715 will allow a minor flow of air to the volume in the distal end of the piston driver. This will result in a minor negative pressure which will cause the flexible material to be sucked out against the interior walls of the first bore 715, thus decreasing the flow of air to the volume at the end of the piston driver even further. The flexible element 761 will therefore along with the piston driver 710 act as a damper which will slow down the speed of the piston driver 710. Hence, the damping mechanism, by exerting a counterforce acting against a driving force exerted on piston driver 710, an effective limit of the speed of the piston driver is provided as long as the flexible element 761 engages the first bore 715 of piston driver 710.

As the cartridge reaches the position in which it is connected to the needle (shortly after the state shown in FIG. 13*a*, middle image), the piston driver 710 reaches a position in which the walls of the first bore 715 transforms into the walls of the second bore 716, i.e. the internal walls of the piston driver widens to a diameter larger than the flexible element 761, which means that the dampening effect is removed (see FIG. 13*a*, right image). This ensures that no damping effect is exerted on the piston driver 710 as the medicament is ejected from the cartridge 600, thus ensuring sufficient force to eject the medicament.

The injector may be adapted to release the damping effect close to the state where the rear needle 520 is fully inserted into the septum 620 of cartridge 600. However, the damping mechanism may in other embodiments be configured to be released at other stages of the movement of the piston driver 710 such as during the insertion of the rear needle 520 into the septum 620 or even before the tip of the rear needle 510 enters into contact with the septum 620. Alternatively, the damping mechanism may be configured for release shortly after movement of the piston 630 relative to the remaining parts of cartridge 600 has been initiated.

While the above damping mechanism has been shown as involving both pneumatic and frictional forces, other damping mechanisms may involve only one of the two types of dampening forces. Alternatively other types of damping forces such as hydraulic dampening forces may be used. In addition, it is understood that in other embodiments, the position of the elements making up the damping mechanism may be reversed and that the location of the elements may be arranged differently on the parts which move relatively during the forward movement of the cartridge for damping impact between cartridge and needle assembly. For example, a damper may be provided on a cartridge holder for damping movements between the cartridge holder and the device housing. For the injection device 100' of the second embodiment, a damping mechanism may be provided between needle assembly 350' and piston driver 310'. The damping mechanism described above may be incorporated in injection devices which include a stored energy source such as a pre-strained spring or in devices where a user of the device delivers the force which acts on the piston driver for moving the piston driver forwards.

Some preferred embodiments have been shown in the foregoing, but it should be stressed that the invention is not limited to these, but may be embodied in other ways within the subject matter defined in the following claims.

The invention claimed is:

1. An injection device comprising:
    a medicament cartridge having a medicament, a cartridge septum adapted to be pierced by a needle for establishing fluid communication with a cartridge interior, and a slideably arranged piston which is driveable towards the cartridge septum,
    a piston driver capable of driving the piston towards the cartridge septum,
    a needle unit having a front needle for penetrating skin of a subject user and a rear needle for piercing the cartridge septum, the front needle and the rear needle being adapted for fluid communication, the cartridge and the rear needle being configured for relative movement from a first state where the cartridge septum is sealed to a second state where the cartridge septum is pierced by the rear needle,
    a needle shield associated with the needle unit, the needle shield and the front needle being configured for relative movement from a shielded state where the front needle is shielded into an unshielded state where the front needle protrudes from the needle shield,
    a holding mechanism associated with the needle unit and the cartridge for releasably maintaining the needle unit and the cartridge in the first state, the holding mechanism being configured to be released upon the front needle being shifted from the shielded state to the unshielded state, and
    an actuator coupled to the piston driver, the actuator providing a stored energy source capable of being released upon release of the holding mechanism to cause the cartridge and the rear needle to enter into the second state where the cartridge septum is pierced by the rear needle and to cause the piston driver to move to dispense the medicament through the needle unit,
    wherein the medicament is dispensed through the needle unit by first forcing the needle shield against an injection site while manually exerting a pushing force on a part of the device wherein the pushing force is transferred to a manual force acting on the needle unit causing manual penetration of the front needle into the injection site prior to causing subsequent release of the holding mechanism thereby causing the cartridge and the rear needle to move into the second state and causing the piston driver to move to dispense the medicament through the needle unit,
    wherein manual penetration of the front needle into the injection site occurs before release of the holding mechanism.

2. An injection device as in claim 1, wherein the holding mechanism includes a releasable retainer configured to retain the piston driver relative to the needle unit and configured for release upon relative movement between the needle unit and the needle shield for allowing the piston driver to move relative to the needle unit.

3. An injection device as in claim 2, wherein the holding mechanism further includes a release coupling configured to cause release of said releasable retainer when the front needle protrudes farther from the needle shield than a predetermined distance from the needle shield.

4. An injection device as in claim 1, wherein the holding mechanism is configured for maintaining the rear needle and the cartridge in the first state until the front needle protrudes a predetermined distance from the needle shield and whereupon, when the front needle protrudes farther from the needle shield than said predetermined distance, the holding mechanism is released for shifting the rear needle and the cartridge into the second state.

5. An injection device as in claim 1, wherein the needle unit comprises a sterility barrier for the front needle and/or a sterility barrier for the rear needle.

6. An injection device as in claim 1, wherein the piston driver is attached to the piston of the cartridge.

7. An injection device as in claim 1, wherein the device further comprises an activator, the activator being mechanically associated with the needle unit so that when the activator and the needle shield are moved relative to each other, the activator causes the front needle and the needle shield to move relative to each other.

8. An injection device as in claim 7, wherein the needle unit substantially follows movement of the activator as the activator moves relative to the needle shield.

9. An injection device as in claim 7, wherein the activator defines a housing section which at least partly accommodates said cartridge, the activator being coupled to the needle unit to transfer a force from the activator to the needle unit when the activator is moved relative to the needle shield.

10. An injection device as in claim 7, wherein the needle shield defines a housing section which at least partly accommodates said cartridge, the activator being coupled to the needle unit to transfer a force from the activator to the needle unit when the activator is moved relative to the needle shield.

11. An injection device as in claim 10, wherein a needle shield spring is associated with the needle shield and the needle unit to urge the front needle into the shielded state and wherein an activator spring is arranged between the activator and the needle unit to urge the needle unit away from the activator and wherein a spring constant of the activator spring is greater than a spring constant of the needle shield spring.

12. An injection device as in claim 10, wherein a needle shield spring is associated with the needle shield and the needle unit to urge the front needle into the shielded state.

* * * * *